(12) United States Patent
Kingsley et al.

(10) Patent No.: US 6,871,084 B1
(45) Date of Patent: Mar. 22, 2005

(54) HIGH-IMPEDANCE OPTICAL ELECTRODE

(75) Inventors: Stuart A. Kingsley, Bexley, OH (US);
Sriram S. Sriram, Powell, OH (US);
Anthony A. Boiarski, Columbus, OH
(US); Norman Gantz, Columbus, OH
(US)

(73) Assignee: Srico, Inc., Columbus, OH (US)

( * ) Notice: Subject to any disclaimer, the term of this patent is extended or adjusted under 35 U.S.C. 154(b) by 447 days.

(21) Appl. No.: 09/898,402

(22) Filed: Jul. 3, 2001

Related U.S. Application Data
(60) Provisional application No. 60/215,918, filed on Jul. 3, 2000.

(51) Int. Cl.[7] ............................................... A61B 5/04
(52) U.S. Cl. .................................... 600/372; 398/183
(58) Field of Search ........................ 600/372; 398/183; 359/160, 161, 173, 183, 189, 154, 279; 385/2, 3

(56) References Cited

U.S. PATENT DOCUMENTS

| 5,287,212 A | * | 2/1994 | Cox et al. ................... 398/183 |
| 5,359,447 A | * | 10/1994 | Hahn et al. .................. 398/201 |
| 5,687,018 A | * | 11/1997 | Funaki ........................ 359/245 |
| 5,739,936 A | * | 4/1998 | Yakymyshyn et al. ...... 398/145 |
| 5,751,867 A | * | 5/1998 | Schaffner et al. .............. 385/3 |
| 5,995,685 A | * | 11/1999 | Seino ............................. 385/3 |
| 6,341,184 B1 | * | 1/2002 | Ho et al. ........................ 385/3 |
| 6,356,680 B1 | * | 3/2002 | Kirk et al. .................... 385/29 |
| 6,359,716 B1 | * | 3/2002 | Taylor ........................ 398/212 |
| 6,370,290 B1 | * | 4/2002 | Ball et al. ..................... 385/14 |
| 6,479,979 B1 | * | 11/2002 | Kingsley et al. ............. 324/96 |

* cited by examiner

Primary Examiner—Roy D. Gibson
(74) Attorney, Agent, or Firm—Kremblas, Foster, Phillips & Pollick

(57) ABSTRACT

High-impedance optical electrodes modulate light in response to a life-form bio-potential and then converts the modulated light to an electrical signal that provides traditional EEG and EEC type output. Light splitters are used to provide multiple electrodes and an electronic reference source. A pilot tone is used to achieve high sensitivity and synchronize multiple units while an optical phase-shift modulator is used to reduce optical noise.

56 Claims, 31 Drawing Sheets

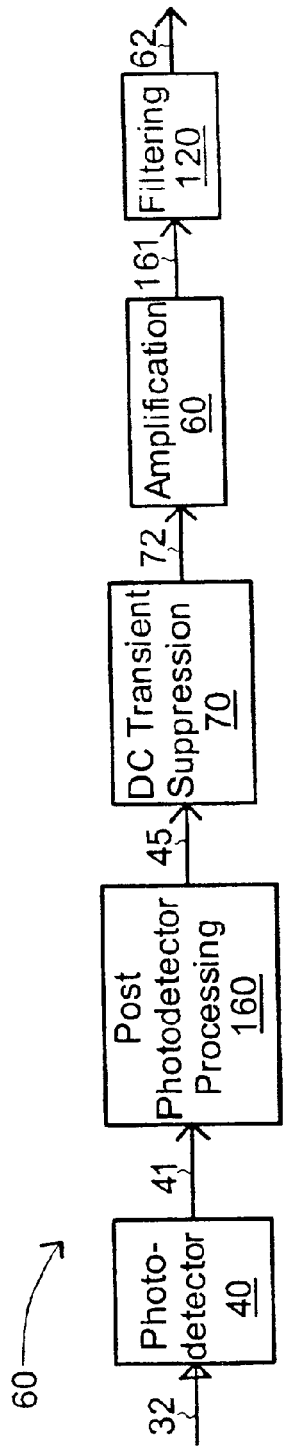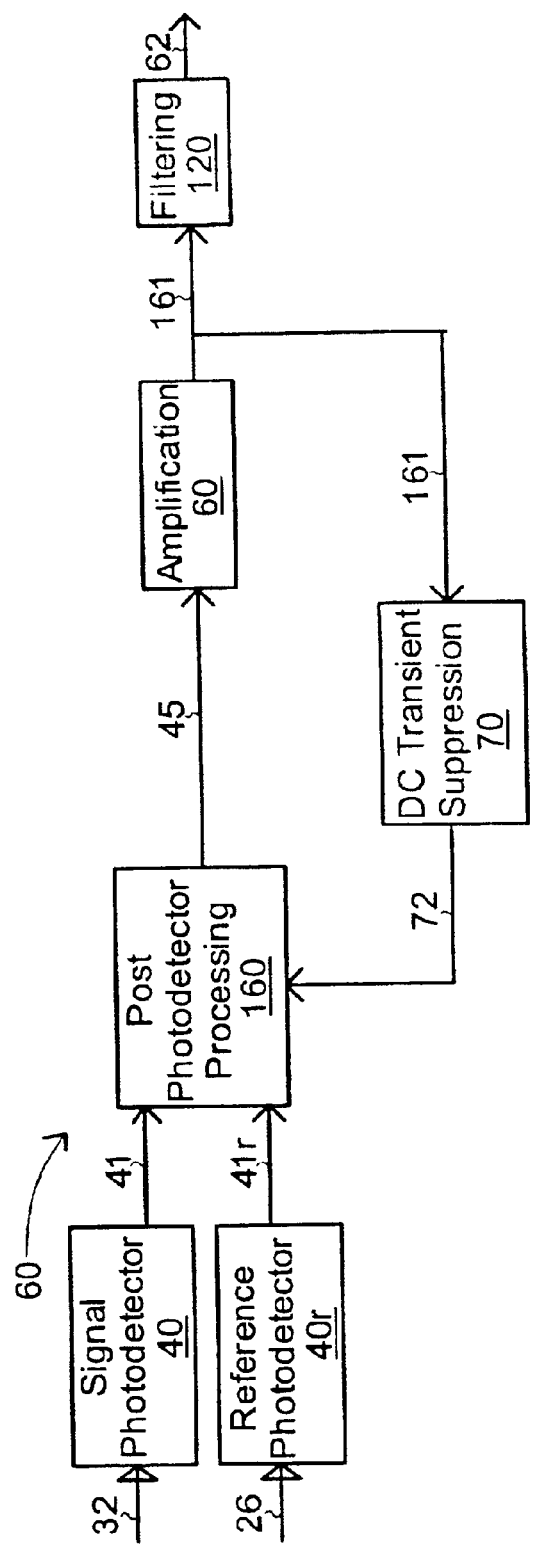

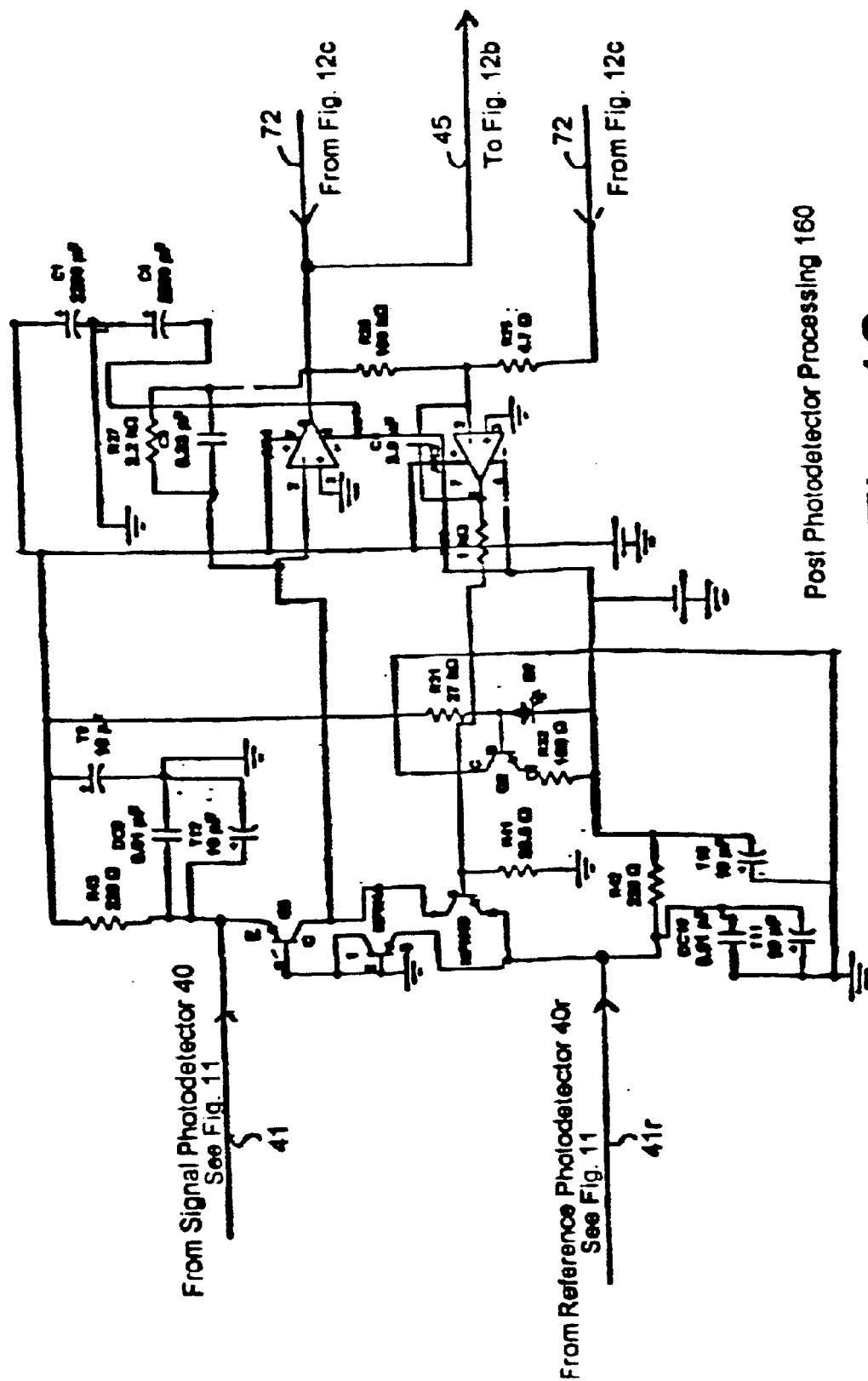

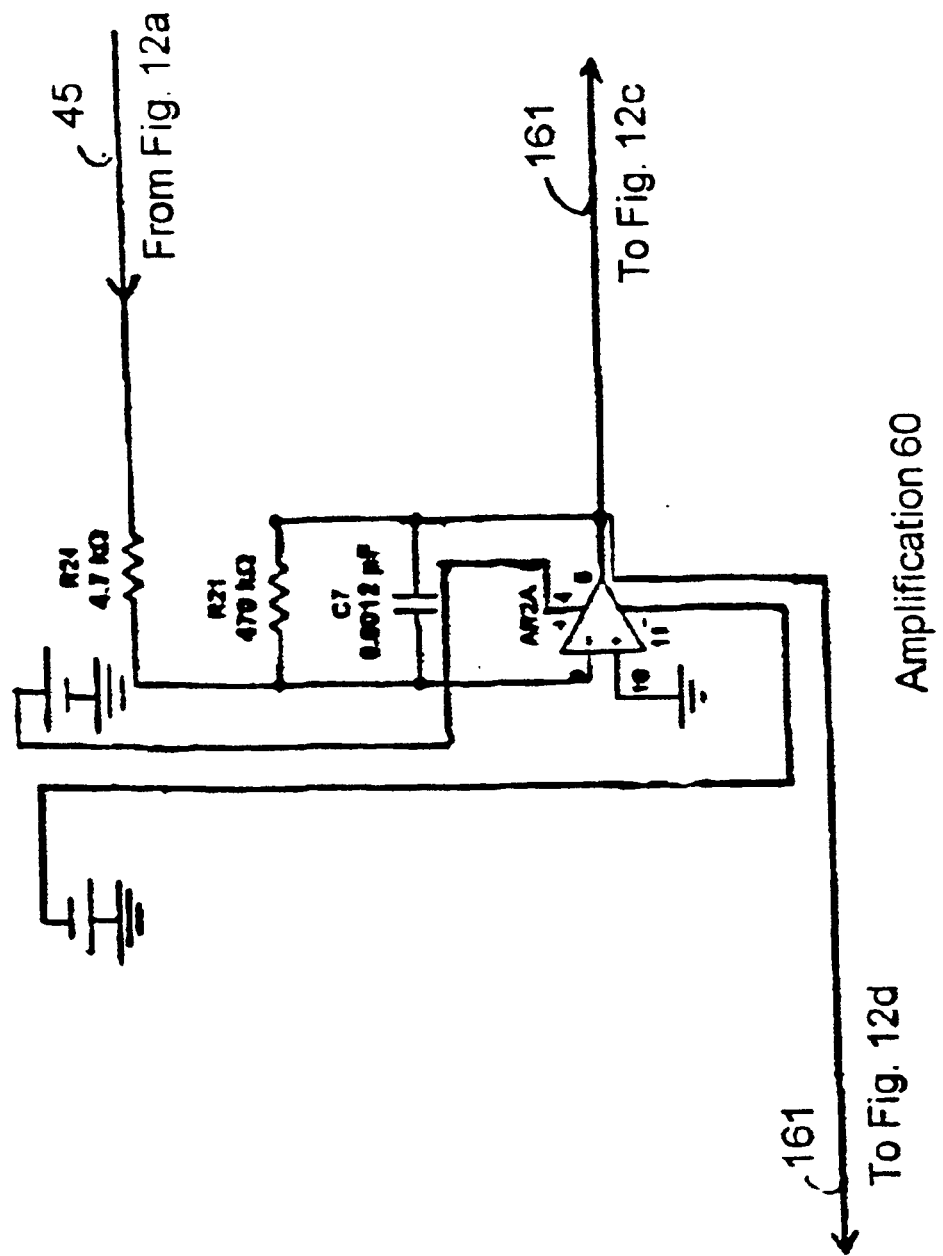

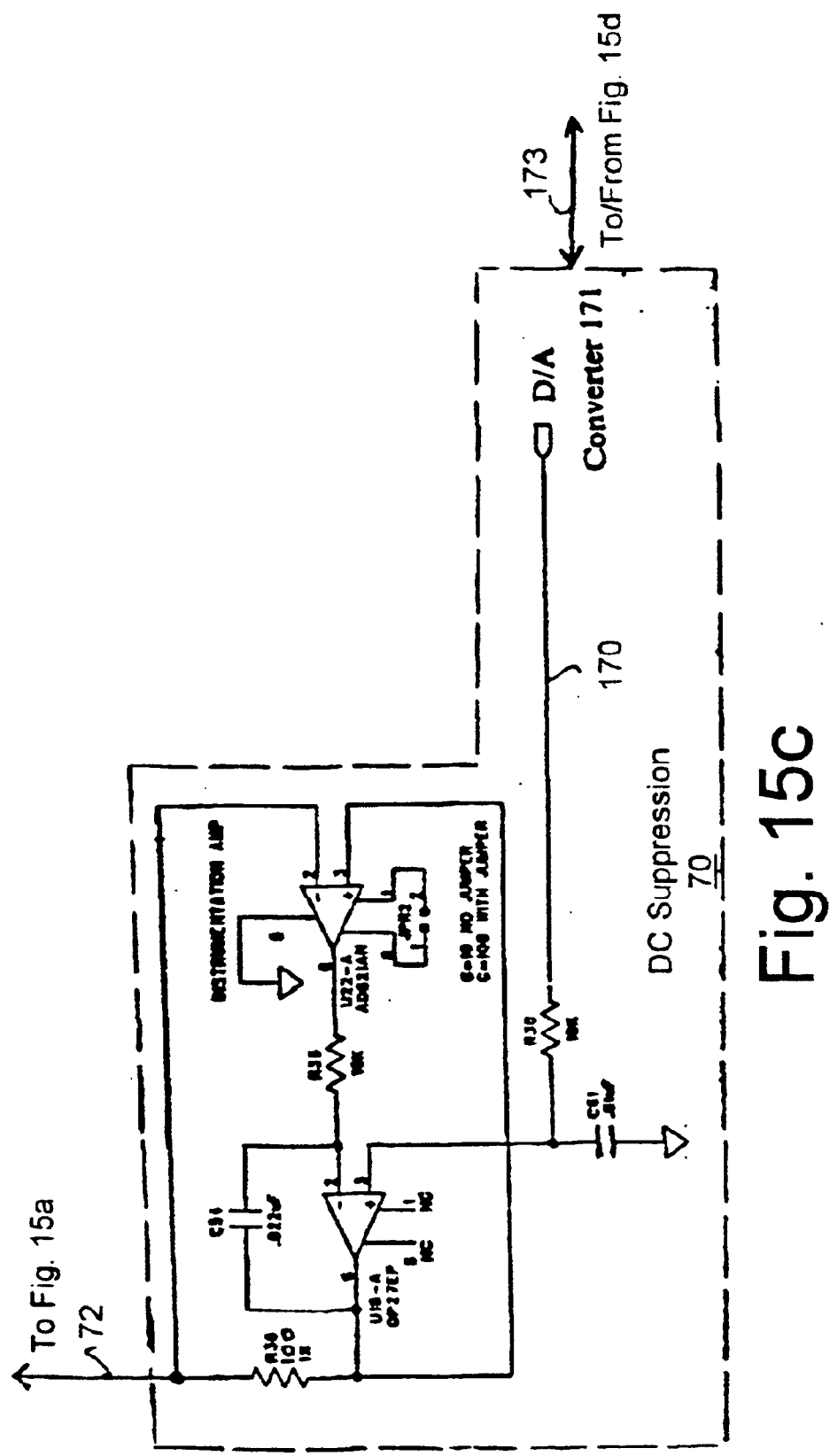

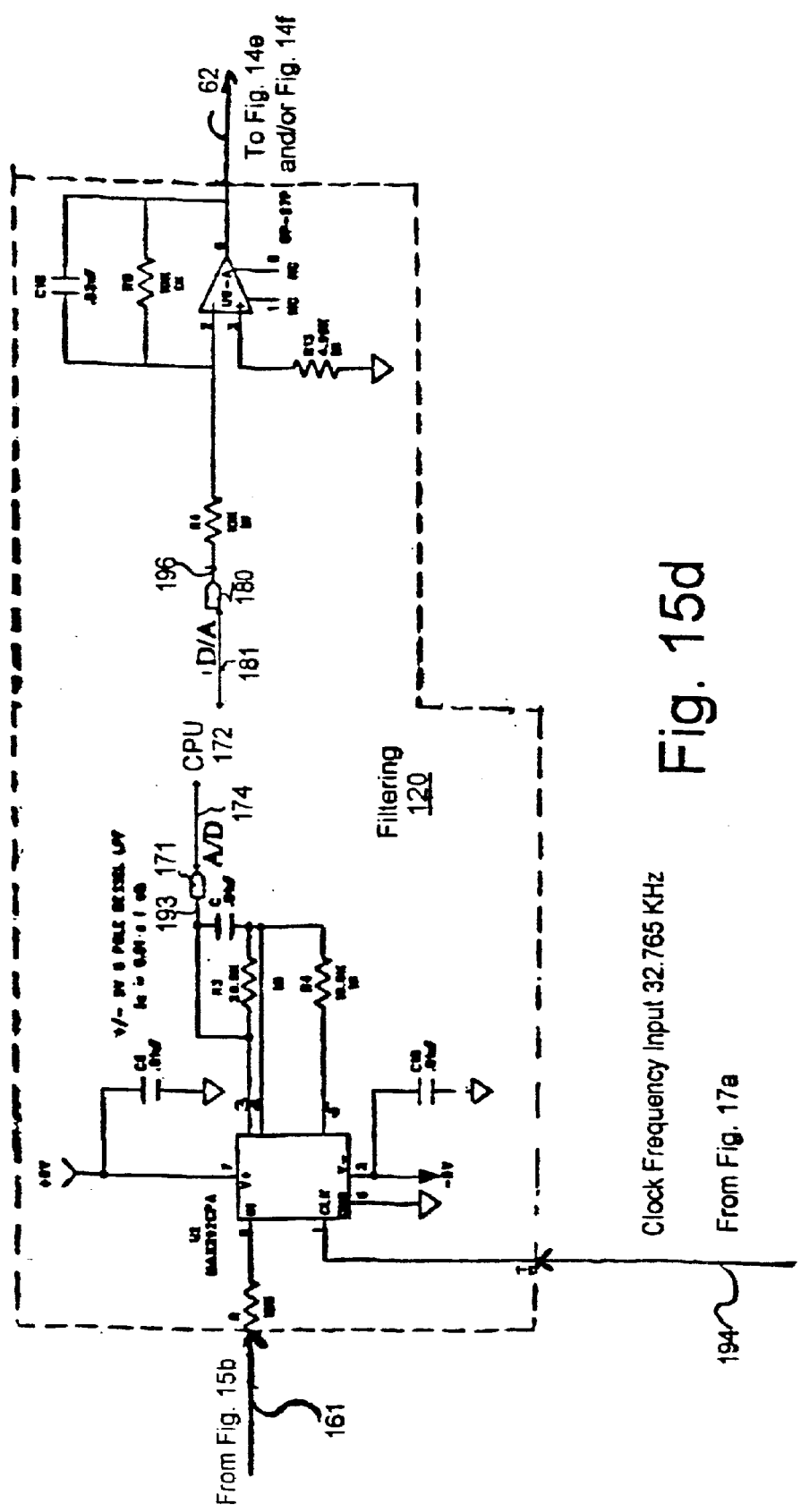

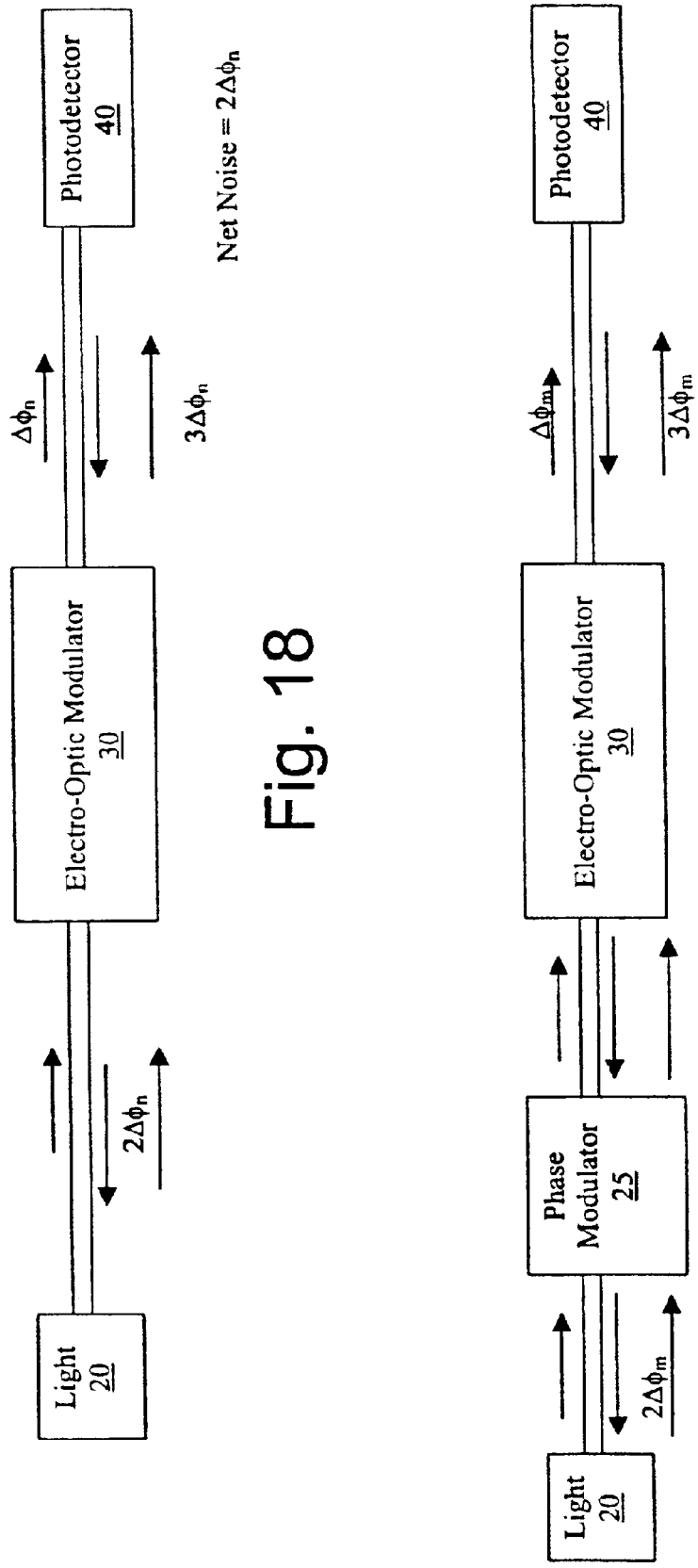

(a) Phase Modulation Index = 0 radians (b) Phase Modulation Index = 1.0 radians (c) Phase Modulation Index = 2.405 radians (d) Phase Modulation Index = 4.0 radians

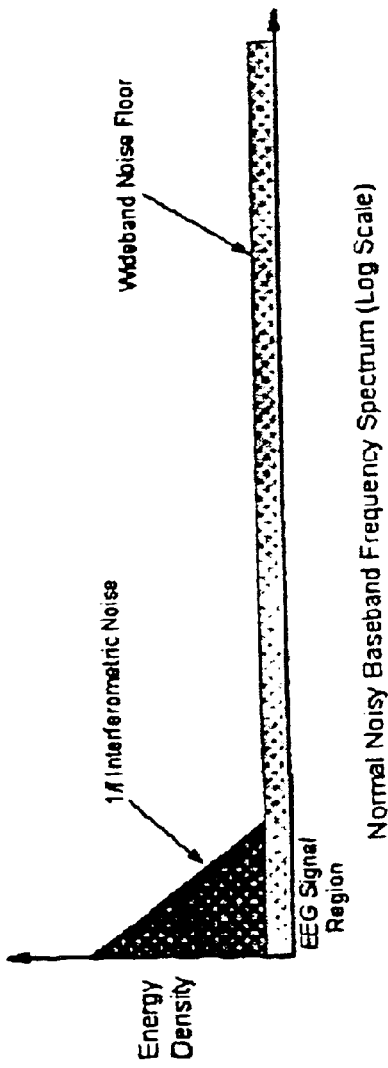 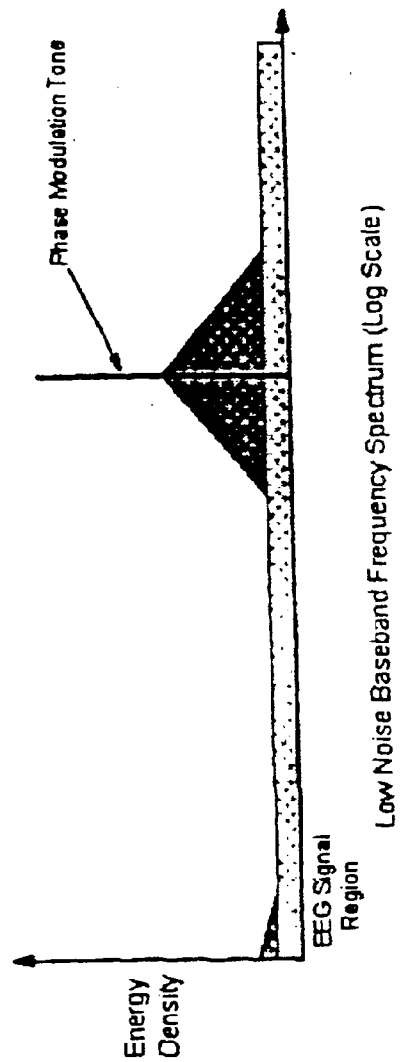

HIGH-IMPEDANCE OPTICAL ELECTRODE

CROSS REFERENCE TO RELATED APPLICATION

This application claims the benefit of U.S. Provisional Application 60/215,918 filed on Jul. 3, 2000 all of which is incorporated by reference as if completely written herein.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of contract No. DAMBI7-98-C8008 and 8009 awarded by the U.S. Army Medical Research and Material Command.

BACKGROUND OF THE INVENTION

1. Field of the Invention

The present invention relates, in general, to electrodes used in the measurement of bio-potential signals produced by living bodies and more particularly to high-impedance electrodes for transferring bio-potential signals from the body to output and/or recording devices without special skin preparation or use of electrolyte gels.

2. Background of the Invention

Various tissues exhibit electrical activity resulting in bio-electric signals that travel throughout the body. The purpose of this signal transmission is to distribute information from one part of the body to another when a necessary function is being carried out. For example, tissues such as nerves, sensory organs, and muscles exhibit such electrical phenomena. The result of this electro-physiological activity is the presence of various bio-electric voltages (i.e., bio-potentials) that exist throughout the body and on its surface. The surface signals are routinely recorded and interpreted to provide non-invasive information regarding the physiological state of an individual.

In the heart, for example, electrical signals coordinate the rhythmic pumping of the cardiac muscles and the bio-potential signals resulting from the heart's electrical activity are routinely recorded. This record of the well-coordinated electrical events that take place within the heart is called an electrocardiogram (ECG).

The brain also exhibits electrical activity that occurs mainly in the cerebral cortex. The electric potentials, measured on the scalp, are called brain waves and the recorded brain activity, as a function of time, is called an electroencephalogram (EEG). Under many conditions, multiple neurons within the cortex fire simultaneously producing an asynchronous signal with little information content. However, when the input to a region in the brain is synchronous with the electrical activity occurring at the same time, rhythmic EEG signals, with various amplitude and frequency content, are obtained from different regions of the brain. Such regions include the frontal, occipital, temporal, and parietal lobes.

Clinically, the EEG and ECG techniques are both currently used to diagnose a number of physiological conditions. In the clinical ECG, three to twelve electrodes are attached to the chest to obtain detailed information related to the state and condition of the heart. The status of heart muscles (e.g., potential ischemia) is often determined and various life-threatening heart arrhythmias are routinely identified. In the case of the clinical EEG, up to twenty-six (or more) electrodes are attached to the patient's scalp and forehead. The resulting EEG bio-potential signals are examined as a means to indicate diseased brain tissue, and identify potential brain tumors. EEG has also been used extensively to diagnose sleep disorders, and in the diagnosis and treatment of specific types of epileptic conditions. There is also a desire to obtain EEG signals from patients suspected of having a stroke as the EEG data could provide an early indication of the type of stroke. This information could also help select and guide specific treatment modalities.

Monitoring the small-amplitude EEG and ECG signals currently requires use of contact electrodes that are physically attached to the body surface. Further, an electrolyte gel is needed as an interface between the skin and the electrode material. The gel provides what is often referred to as a wet contact with low electrical impedance. The low impedance is required to minimize noise pickup from the surrounding environment as well as small movements from the individual.

Currently, there are a number of companies that provide a variety of ECG instruments for medical research and clinical practice. Use of the ECG is especially widespread and the equipment is highly advanced. There are sophisticated diagnostic ECG instruments, monitoring devices for routine use for a variety of medical environments and even portable (i.e., credit-card size) devices. The portable instruments are used for ambulatory ECG monitoring as well as in fitness and exercise programs.

Evaluation of ECG data is relatively straightforward and highly advanced. With little training, most medical staff can obtain a good deal of information from the ECG signals. Automated, computer analysis is available to assist the Cardiologist in diagnosing various heart abnormalities. Because of the nature and convenience of obtaining and interpreting the ECG signals, almost every patient in an operating room (OR), intensive care unit (ICU), or ER environment is routinely monitored with ECG equipment.

Equipment for EEG monitoring is also available from several manufacturers. The recording of EEG bio-potentials is, on the other hand, currently reserved more for research purposes and in some specific diagnostic situations. EEG data is only sporadically used for monitoring in the ER/ICU environment. Because of the complex nature of the multiple EEG signals, a specialist must normally analyze EEG measurements.

Recently a device, called the BIS (Bispectral Index) monitor has been introduced that uses EEG signals to determine a patient's hypnotic state in the OR environment. In this case one sensor comprised of three disposable electrodes is coated with electrolyte gel and attached to the patients' forehead. A special electronics unit provides a single, macro-EEG output that is indicative of the state of anesthetic hypnosis. This output corresponds to a numeric unit from 0–100 indicating an absence of brain activity to maximum brain activity respectively.

Shortcomings in the current ECG and EEG measurement approaches are mainly related to electrode/electrolyte gel attachment. In the ECG case, the electrode (with electrolyte gel) is kept in contact with the skin using a special, disposable adhesive patch. The electrodes are relatively simple to attach and easy to remove. If body hair is present, however, attachment and removal can be problematic. In most cases, good ECG recordings can be obtained, but the attachment site must be on bare skin (i.e., the upper-body clothing must be removed) and the electrode attachment site often must be cleaned using rubbing alcohol. Up to twelve electrodes are used for detailed diagnosis of the heart's electrophysiology, but only two or three are needed for general monitoring of the heart in an operating room (OR), intensive care unit (ICU), or emergency room (ER). Finally, most medical staff can quickly and correctly attach an ECG electrode with a minimum amount of operator training.

Attachment of EEG electrodes, on the other hand, introduces a new set of problems to medical staff wanting to use this technology, namely:

1) The electrodes are often made of materials such as gold or silver preventing routine disposal. This means that the electrodes must be cleaned before and after use by each patent.
2) The patients' scalp must be cleaned using a relatively strong solvent, such as acetone, and mildly abraded prior to application of the cup-shaped electrode filled with electrolyte paste.
3) New electrolyte gel must be applied manually to the electrode prior to attachment for each new patient.
4) Pressure must be applied to the gel-filled electrode-cup assembly to cause adherence to the head. This process is often uncomfortable for the patent.
5) The contact resistance of the electrode to the scalp must often be measured to insure it is less than 1000 ohms otherwise noisy recordings are obtained. This measurement process is time consuming and tedious.
6) During use, the electrolyte gel tends to harden and stick to the hair of the patient. Removal of the electrodes and remnants of the gel from the hair takes some time and effort with much discomfort to the patient.

During use, the electrodes often became dislodged requiring re-attachment. Such difficulties result in the following:

1) A trained technical staff person is normally required to attach the electrodes. Often this technician is not available at all times, so the clinician cannot depend on obtaining the desired EEG data.
2) There is an additional cost factor associated with using trained staff and the current medical reimbursement policies tend to encourage minimal use of trained staff in the hospital environment.
3) The attachment protocol takes a considerable amount of time especially when multiple electrodes are required.
4) The ordeal is difficult and tedious for the patient.

Because of the cost and inconvenience of applying EEG electrodes, it is difficult (if not impossible) to use the EEG for routine patient monitoring. EEG information is, therefore, not normally obtained in the ICU, or ER environment.

Use of Magnetic Resonance Imaging (MRI) machines has become a routine method for obtaining information regarding a patient's anatomy and physiology. Currently, however, not many patients are monitored (except some children) while they are in the MRI using EEG and/or ECG instrumentation. Basically, the MRI and EEG/ECG equipment are not compatible. The operating MRI produces strong radio frequency (RF) fields and large static magnetic fields are always present. These fields induce current flow in electrodes and any attached electrode wires especially if the wires are inadvertently formed in a loop. Some instances of localized skin burns have been reported or a result of electrodes and looped wires residing in MRI machines. Such cases are recognized as macro shock situations, whereby current distribution is diffused throughout the body. Such situations can be fatal if the current induced is sufficiently large.

The presence of equipment near the MRI machine can also interfere with the diagnostic quality of the MRI images themselves by causing distortions in the MRI output. Also, the radio-frequency (RF) fields of the MRI machine can corrupt the weak signals being recorded by ECG equipment and especially even weaker signals associated with EEG instruments. For this reason, a special screen room is built around the MRI machine to prevent it from affecting equipment in the vicinity of the imaging device. Generally, MRI test patients have all electrodes removed from their body and all unnecessary equipment is kept outside the MRI screen room.

To solve these and other associated problems with prior art bio-potential measuring electrodes, it is an object of the present invention to provide a device that avoids a macro shock situation.

It is an object of the present invention to provide easy set up for measuring bio-potentials.

It is an object of the present invention to optimize a patient's comfort level during the bio-potential measurement process.

Also, it is an object of the present invention to eliminate the use of electrolytic paste during bio-potential measurement.

It is an object of the present invention to minimize patient preparation for bio-potential measurement.

It is an object of the present invention to avoid patient removal of hair or clothes.

It is an object of the present invention to provide standard clinicians and hospital employees with a bio-potential measurement device that is easy to use without extensive training.

It is an object of the present invention to provide multiple small sized bio-potential sensors that can be fit into small areas.

It is an object of the present invention to minimize electromagnetic interference (EMI) noise.

It is an object of the present invention to provide a bio-potential measuring instrument with low power consumption.

It is an object of the present invention to provide a bio-potential device that can be used at various frequencies.

It is an object of the present invention to provide an output that interfaces with standard amplifiers, filters, hardware devices, and computer software.

It is the object of the present invention to provide a bio-potential sensor that is re-useble.

SUMMARY

To meet these objects, the present invention features a high impedance optical-based electrode. In the past, those skilled in the art were of the notion that to improve the monitoring various electrical signals (bio-potential signals), good electrical contract between the subject and the electrode were essential to produce a good output signal, that is, a signal that clearly represented the actual electrical phenomenon occurring within the body. To this end, the skin was abraded to remove dead cells and special electrically conducting pastes were applied to reduce the impedance as much as possible, i.e., the total opposition of flow of the alternating current generated by the body as bio-signal moved from the heart or brain to the recording or display instrument. Typically this resistance to bio-signal flow (the real part of the electrode impedance) was reduced to a few thousand ohms.

The present invention features an electrode that operates with a resistance to electrical current flow (real part of the electrode input impedance) of more than $1 \times 10^{14}$ ohms, (100 tera ohms, that is, 100,000,000,000,000 ohms or a hundred trillion ohms) of resistance. To achieve such a high real input impedance, the electrodes of the present invention features the use of interferometers such as a Mach-Zehnder interferometer to take advantage of the high-frequencies of light which vibrates at frequencies in the tera-hertz range, that is, from $10^{11}$ to about $10^{16}$ cycles per second (100,000,000,000 to 1,000,000,000,000 cycles per second) as opposed to the body potentials operating at less than a few hundred cycles per second.

A light interferometer according to the present invention typically divides light into two paths and then uses the bio-potential from the body to change the optical length of one or both paths so that the light in one path when combined with the light in the second path interferes with the light in the other path to produce a change in the intensity of the original incoming light. Because of its compact size, integrated components, and stable operating characteristics, a Mach-Zehnder type interferometer is preferred for use in the present invention although it is to be realized that other light interferometers including bulk component devices can be used. By operating the Mach-Zehnder interferometer at the mid-point of its optical output range, the changes in light intensity vary linearly with the bio-potential that is being measured. Light having these changes in light intensity, i.e., light modulated by the bio-potential leaves the Mach-Zehnder interferometer and is typically converted into an electric potential by an optical receiver. The output voltage can be used in conventional display and recording devices to produce the desired output trace or plot. Alternatively the modified light can be output and optically amplified to provide basic bio-potential data, e.g., a visual light output of the heart beat. In order to reduce environmental changes such as humidity, the present invention features a hermetic housing to stabilize the electro-optic material that serves as the basis of the interferometer, e.g., the Mach-Zehnder interferometer.

In its basic form the high impedance optical electrode of the present invention comprises 1) a light source typical with a coherent light component as found in a laser diode; 2) an electro-optic material that a) receives light from the light source, b) modulating the light from the light source in response to a bio-potential that is being measured, and, as a result, c) provides a modulating light output; and 3) an optical receiver that receives the modulated light and converts it to a voltage that is proportional to the bio-potential.

The optical receiver and the light source can be both connected to the electro-optic material with optical fibers. Alternatively the optical receiver can be connected directly to the electro-optic material.

The electro-optic material is typically used in the form of an integrated Mach-Zehnder interferometer operating in the linear region. The interferometer is enclosed or sealed in a housing to protect it from environmental factors that could change its sensitivity.

A sensor is used to convey the bio-potential to an electrode formed on the interferometer. The sensor can be formed of any electrically conducting material, but for patient comfort an electrically conducting silicon rubber is preferred. The rubber is formed with an irregular surface, e.g., a saw-tooth surface for penetrating hair and avoiding the need to remove such hair prior to taking the bio-potential scan. The high impedance electrode is capable of picking up the bio-potential of interest without resort to the use of conductive ointments and gels or even the need of the patient having to remove his or her clothing.

The present invention also features a number of electrical circuits for improving performance including a super low-noise optical receiver circuit, an amplifier circuit, a DC transient suppression circuit, a filtering circuit, and an automatic gain control circuit using an out-of-range pilot tone.

The foregoing and other objects, features and advantages of the invention will become apparent from the following disclosure in which one or more preferred embodiments of the invention are described in detail and illustrated in the accompanying drawings. It is contemplated that variations in procedures, structural features and arrangement of parts may appear to a person skilled in the art without departing from the scope of or sacrificing any of the advantages of the invention.

BRIEF DESCRIPTION OF THE DRAWINGS

FIG. 9 is a schematic block diagram illustrating the major components of the electronic circuitry of the high-impedance optical electrode including the photodetector, post-photodetector processing circuitry, DC transient suppression circuitry, amplification circuitry, and filtering circuitry.

FIG. 11 is a schematic block diagram illustrating the arrangement of the major components of the electronic circuitry (reference and signal photodetectors, post-photodetector processing circuitry, DC transient suppression circuitry, amplification circuitry, and filtering circuitry) when a noisy laser is used.

FIG. 12a is a detailed schematic of the post-photodetector processing block shown in FIG. 11.

FIG. 12b is a detailed schematic of the amplification processing block shown in FIG. 11.

FIG. 15c is a detailed schematic of the DC transient suppression block shown in FIGS. 13 and 14.

FIG. 15d is a detailed schematic of the filtering block shown in FIGS. 13 and 14.

FIG. 18 is a schematic diagram illustrating the net noise associated with the back-reflection of light in an electro-optic modulator system.

FIG. 22 is a schematic diagram illustrating the net modulation associated with the back-reflection of light in an electro-optic modulator system.

FIG. 24(a) illustrates the level of noise with no phase modulation while FIG. 24(b) shows 1.0 radian of phase modulation, 24(c) shows 2.405 radians of modulation while 24(d) shows 4 radians of modulation.

FIGS. 25(a) and 25(b) illustrate the level of noise associated with an EEG signal both with and without a phase modulation tone, FIG. 25(a) showing no modulation while FIG. 25(b) illustrates the effect of the use of a phase modulation tone.

Figure 1:
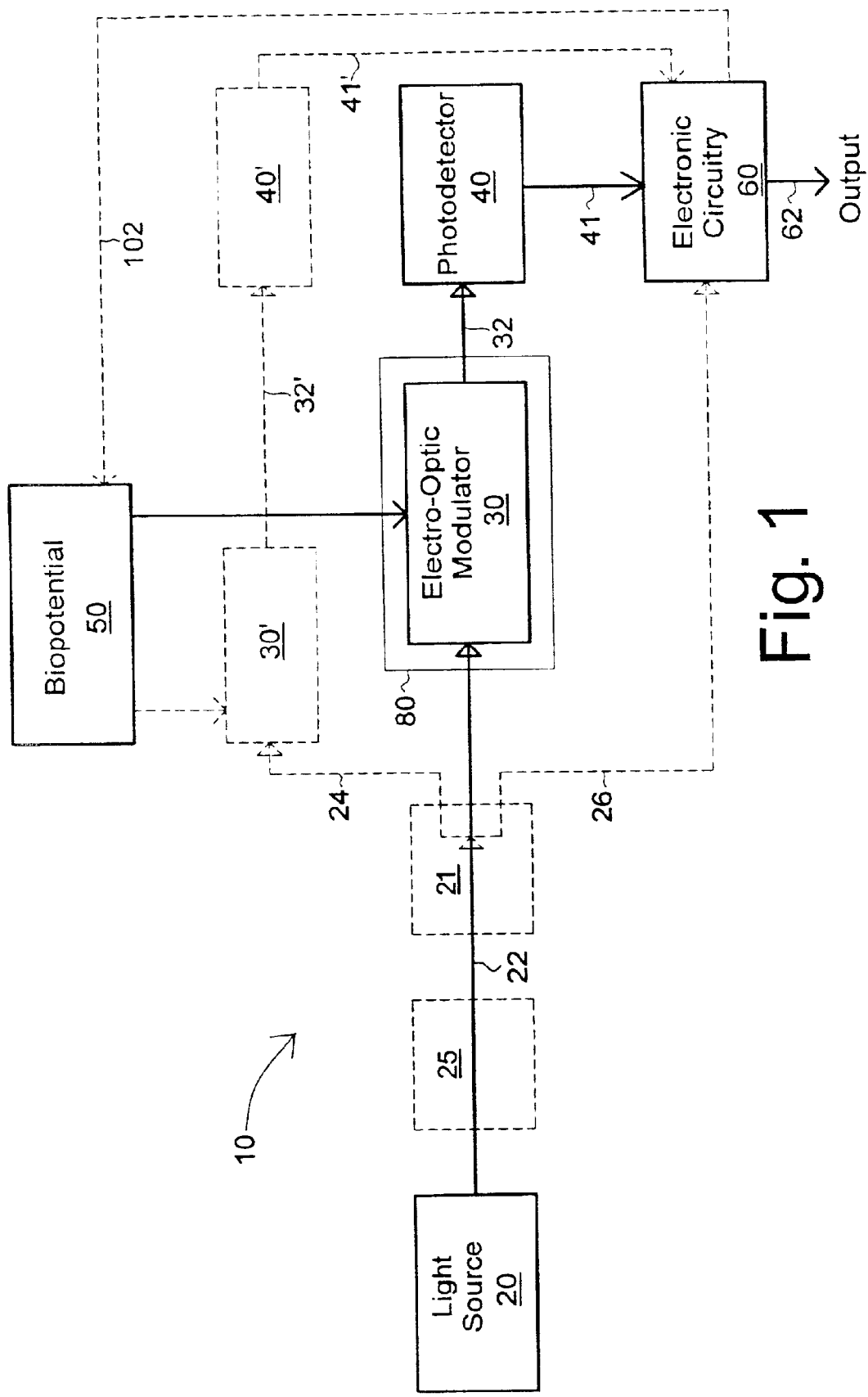
FIG. 1 is a schematic block diagram of the present invention illustrating its major components including a light source, electro-optic modulator, photodetector, and electronic circuitry.

In describing the preferred embodiments of the invention which are illustrated in the drawings, specific terminology is resorted to for the sake of clarity. However, it is not intended that the invention be limited to the specific terms so selected and it is to be understood that each specific term includes all technical equivalents that operate in a similar manner to accomplish a similar purpose.

Although preferred embodiments of the invention have been herein described, it is understood that various changes and modifications in the illustrated and described structure can be affected without departure from the basic principles that underlie the invention. Changes and modifications of this type are therefore deemed to be circumscribed by the spirit and scope of the invention, except as the same may be necessarily modified by the appended claims or reasonable equivalents thereof.

DETAILED DESCRIPTION OF THE INVENTION AND BEST MODE FOR CARRYING OUT THE PREFERRED EMBODIMENT

With reference to the drawings and initially FIG. 1, the present invention, a high-impedance, optically-based electrode, is generally designated by the numeral 10. As with conventional bio-electrodes, the purpose of the electrode of the present invention is to serve as an interface between an animal life form (typically referred to as a patient) and the various electrical potentials produced by that life form, i.e., bio-potentials, and the various recording, display and analysis devices which process the bio-potential for recording, analysis, and display purposes. In its basic form, the present invention consists of an electro-optic modulator 30 that receives light 22 from a light source 20 and changes the light 22 in response to a bio-potential 50 of the patient. In its basic form, the electro-optic modulator 30 is a material such as a polymer or crystal that changes the form (property) of light 22, i.e., modulates the light, in response to bio-potential 50. This change in light form (modulation) can be a change in polarization, phase, intensity or a combination of these properties. The changed, i.e., modulated, output light 32, that emerges from the electro-optic modulator 30 is proportional to bio-potential 50.

As a simple illustration of the device, visible light 22 from light source 20 passes through the electro-optic modulator 30 without change in the absence of a bio-potential. However, when electro-optic modulator 30 is placed in the presence of a bio-potential, e.g., positioned near the heart of a patient, the changes in bio-potential produced by the heart as it beats causes modulator 30 to change (modulate) the light. For example, if the intensity of the light is the light property being changed under the influence of the bio-potential, the light 32 emerging from modulator 30 is observed by the naked eye to become brighter (or darker) with each beat of the heart. Thus in this basic form, one can determine the heart rate of the patient by counting the number of changes in light intensity per unit of time.

Using conventional optical amplifiers, one can further enhance the optical characteristics of the emerging light 32 from modulator 30. Typically, however, it is desirable to transform the modulated light 32 into an electronic signal in order to take advantage of electronic components that provide pen recordings, monitor displays, and electronic database records of the bio-potential. To this end, the present invention features a photodetector 40 by which modulated light 32 is converted to an electrical signal 41. Specifically photodetector 40 produces an electronic signal 41 in response and proportional to the modulated light output 32. Although photodetector 40 could generate an electrical voltage directly from the modulated light 32 in a fashion similar to that found in solar cells, preferably the modulating light 32 is used to control the flow of current in a circuit by means of a photodiode. That is, the change in light intensity is used to increase or decrease the amount of current flowing in the detection circuit.

Once converted into an electronic form, signal 41 is processed by electronic circuitry 60 to provide the desired electronic output signal 62, e.g., an output form that can provide an electronic database record, a printed readout, or an electronic monitor display. As will be discussed, the electronic circuitry 60 comprises amplification, filtering, and DC transient suppression circuitry similar to that used with conventional bio-electrodes as well as circuitry to accommodate the optical aspects of the high-impedance electro-optic electrode.

Because many bio-potentials have multiple inputs, e.g., the brain waves on the surface of the brain as recorded in an electroencephalogram (EEG), the present invention provides for the use of multiple high-impedance optical electrodes. To this end and as shown in phantom in FIG. 1, the present invention features an optical splitter 21 that is used to split light 22 from the light source 20 into two more additional light portions 24 and provide them to modulators 30' and associated detectors 40'. In addition to providing light 22 for additional modulators 30' and detectors 40', splitter 21 can also provide a light portion 26 which is used when it is desirable to provide an optical reference signal to the electronic circuitry 60.

Because certain light sources 20 can produce undesirable noise concentrated at the same frequency as the bio-potential 50, the present invention features an optional phase-shift module 25 that is used to facilitate the separation of noise from the bio-potential signal, especially when a highly coherent laser is used as light source 20. Although the positioning of the phase-shift module in the light path is not critical, that is, module 25 may be placed between light source 20 and electro-optic modulator 30 or between the electro-optic modulator 30 and photodetector 40, preferably when multiple electro-optic modulators 30, 30' are used, placement of phase modulator 25 before optical splitter 21 obviates the need for multiple phase-shift modulators 25 and also insures uniform phase modulation to each of the electro-optic modulators 30, 30'.

To ensure equal sensitivities among multiple electro-optic modulators 30, 30', a pilot tone 102 is generated by the electronic circuitry 60 and superimposed on the bio-potential and subsequently also on the resulting modulated light 32, 32' and electronic signal 41, 41'. By comparing the original pilot tone 102 produced by circuitry 60 with the tone superimposed on the electronic signal 41, 41', it is possible to align multiple electro-optic devices to provide identical and constant sensitivities.

For a single high-impedance optical electrode 10, the light source 20 and photodetector 40 can be attached directly to the electro-optic modulator to afford a compact unit that is readily attached to the electronic circuitry 60 by means of suitable electronic cabling and connectors. However, in certain situations, strong electro-magnetic fields such as those produced by MRI machines can induce sufficient electrical current flow in electrical conductors so as to cause localized burns in the patient. Such problems in the past have made it virtually impossible to monitor electronically a patients vital bio-potentials. By transmitting unmodulated lighted light 22 and modulated light 32 to and from the electro-optic modulator 30 by means of optical fibers 28 and 38, respectively (FIGS. 2, 3 and 7), it is now possible using the current invention to place all electronic cable and circuitry remote to high electromagnetic fields such as those produced by MRI without fear of harm to the patient. Not only is the potential for harm eliminated but the optical fiber connections allow the high-impedance electrodes of the current invention to be used in a highly electromagnetic field environment to achieve real time monitoring of the patent's bio-potentials. Typically the optical fiber that carriers the unmodulated light 22 to the electro-optic modulator 30 is of the polarizing maintaining (PM) type while the optical fiber that carrier modulated light 32 away from the electro-optic modulator is of the single mode (SM) type.

Conventional wisdom has always taught that a low impedance electrode is necessary to obtain a good bio-potential reading from a patient, that is, good electrical contact has to be achieved to allow a small amount of electrical current to flow between the patient and the measuring circuit. As such, the goal for good bio-electrodes has always been to render the impedance as low as possible. Contrary to conventional wisdom, the present invention uses the very high frequency properties of light to achieve a highly sensitive bio-electrode that operates in the tera ohm impedance range. This high-impedance electrode allows for bio-potential measurement without the cleaning, abrading, and conductive pastes used with prior art electrodes. Rather the present invention allows for bio-potential measurement without physical contract, e.g., though the patient's clothing.

The Electro-Optic Modulator 30

A wide variety of electro-optic modulators 30 can be used with the present invention including both bulk and integrated devices. Such devices are based on the polarization, phase, or amplitude modulation of light. Because of the large amount of space and the expense along with the constant need for continual adjustment associated with bulk component devices, integrated devices are preferred to their bulk counterparts. Because photodiodes are particularly effective at controlling the amount of current in a circuit in response to changes in light intensity, Michelson-type interferometers are particularly effective for the present invention. Michelson interferometers split a light beam into two paths that are recombined to afford a certain amount of light interference (loss or gain in intensity) that is indicative of a change in light property in one or both of the split beam paths. One variety of the Michelson interferometer that is used in the present invention is an integrated Mach-Zehnder modulator (interferometer). The Mach-Zehnder modulator produces light intensity changes in the recombined light paths as a result of optical path-length changes occurring in one or both of the split beam paths. Optical path-length changes can be produced in a variety of ways, e.g., a temperature sensor forms the split beam paths in a material that has a high coefficient of thermal expansion, a magnetic field sensor forms the split-beam paths in a magnetostrictive material. Since the present invention is directed to sensing an electrical field, i.e., the electrical field associated with the bio-potential 50, the split beam paths are formed in an electro-optic (piezo-electric) substrate material such as lithium niobate. To create the light paths (waveguides) in the substrate material, a metal such as titanium is diffused into the substrate to form the desired light paths.

Figure 2:
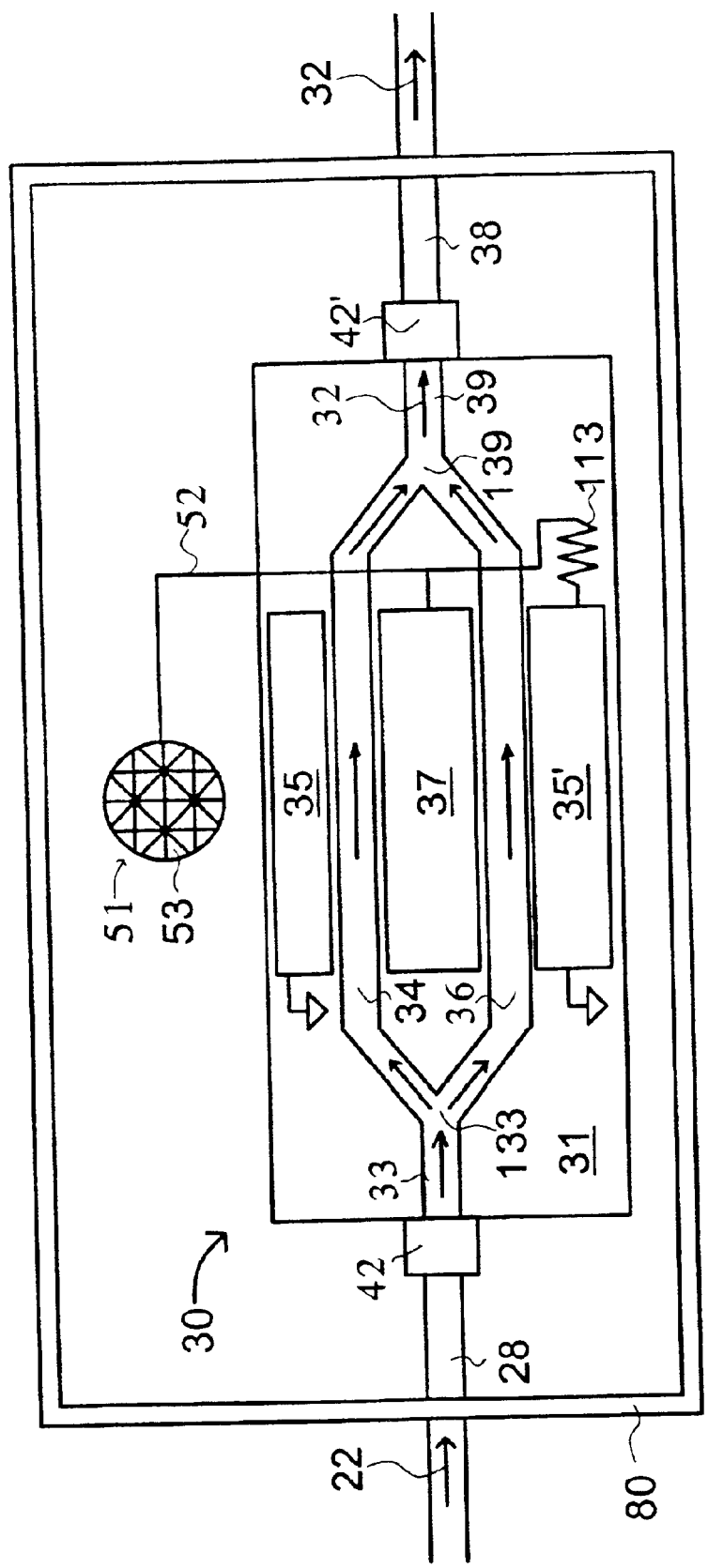
FIG. 2 is a top view of a Mach-Zehnder integrated electro-optic modulator with electronic components illustrated by schematic diagram.

As seen in FIG. 2, the integrated Mach-Zehnder modulator of the present invention comprises a number of waveguides formed in a piezoelectric substrate material 31 such as crystalline lithium niobate ($LiNbO_3$). The waveguides can be formed, for example, by diffusion of a metal such as titanium into the crystal substrate 31. The waveguides include: 1) a light input waveguide 33 that receives light 22 from a light source 20 (FIG. 1), 2) a splitter 133 connected to the input waveguide 33 that receives and splits the light path, 3) a first leg waveguide 34 connected to the splitter 133 and receiving a portion of light 22, 4) a second leg waveguide 36 connected to splitter 133 and receiving a portion of light 22, 5) a combiner 139 for receiving and combining light from first leg wave-guide 34 and second leg waveguide 36 to afford intensity modulated light 32, and 6) an light output waveguide 39 connected to combiner 139 and providing an output for modulated light 32.

Preferably the Mach-Zehnder modulator 30 is designed to operate in the linear region, that is, in a region in which the intensity changes in modulated output light 32 are directly proportional to and vary linearly with the applied bio-potential 50 (FIG. 1). Such operation is achieved by operating the device (without applied bio-potential 50) at the midpoint between maximum brightness of the emerging modulated light (constructive interference) and minimum brightness, i.e., complete (destructive) interference where no light emerges, that is, modulator 30 is operated at the so called quadrature point. When operating at the quadrature point, the modulated output light 32 varies in a linear manner with the applied bio-potential 50 and is directly proportional to it. Quadrature operation is typically set during manufacture by forming the optical path lengths in first leg waveguide 34 and second leg waveguide 36 for midpoint brightness operation, that is, the optical path lengths of leg waveguides 34, 36 differ by a fraction of a wave length, i.e., $\pi/2$ where $\pi$ is the phase change difference associated with an optical path length change necessary to go from minimum to maximum modulated light intensity. Alternately, quadrature can be set by the application of an electrical potential to one or both of the leg waveguides 34, 36 after device manufacture. Additional details as to the construction and operation of Mach-Zehnder devices may be found in many references including U.S. Pat. No. 5,267,336 all of which is incorporated here by reference as if completely written herein.

The electric field of the bio-potential 50 is applied to the waveguide legs 34, 36 with electrically conducting bio-potential plate 37 formed between leg waveguides 34, 36 and grounding plates 35, 35' located on the outsides of leg waveguides 34, 36, respectively. For a waveguide substrate 5 mm wide and 12 mm long and leg waveguides 5 mm long and 7 $\mu$m wide, each of the grounding plates 35, 35' is about 5 mm long and 25 $\mu$m wide while the bio-potential plate 37 is about 5 mm long and 30 $\mu$m wide. The bio-potential and grounding plates 37 and 35, 35', respectively, are typically made of gold and applied using conventional photolithograph processing. The arrangement of the bio-potential plate 37 and the grounding plates 35, 35' shown in FIG. 2 produces a "push-pull" effect on the light in the leg waveguides 34, 36. That is, because the electrical fields are opposite in effect, the light traveling in one of the leg waveguides 34, 36 is retarded, i.e., undergoes a negative phase change, while the light traveling in the other leg waveguide is advanced, i.e., undergoes a positive phase change. Such an arrangement affords increased sensitivity, i.e., a greater amount of intensity change in modulated light 32 than if the bio-electrical potential were applied to only one of the leg waveguides 34, 36. It is to be realized that many arrangements of bio-potential and grounding plates are possible with respect to the waveguide legs of which the arrangement shown in FIG. 2 is but one example.

Figure 3:
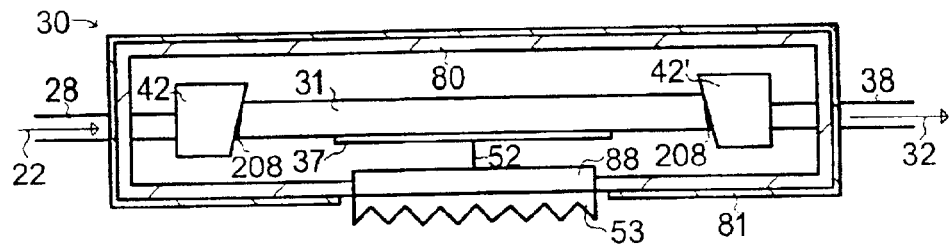
FIG. 3 is a cut away side view of a Mach-Zehnder integrated electro-optic modulator illustrating optical carrier and pick-up pad mounting within the modulator housing.

As shown schematically in FIG. 2 and in side view in FIG. 3, a pick-up pad 51 is used to obtain the bio-potential signal 50 from the patient and transfer it to bio-potential plate 37 by means of electrical conductor 52. Pick-up pad 51 is comprised of a metal substrate 88 which is embedded in housing 80 and to which a conducting rubber 53, typically made of silicon, is applied. The optional contacting rubber 53 is molded in such a way as to produce compliant, saw-toothed protrusions that penetrate hair follicles and make soft, dry contact with the skin and scalp without special scalp preparation and hair removal. It is to be realized that the use of conductor 52, metal substrate 88, and conducting rubber 53 are optional and are intended to minimize patent contact with bio-potential plate 37 for protective reasons, i.e., to avoid damage to the relatively high-cost crystal substrate 31 and gold bio-potential plate 37 by remote contact of plate 37 with the patient through modulator protective housing 80. It is to be appreciated that it is possible to construct the bio-electrode of the present invention by applying the contracting rubber 53 directly to the bio-potential plate 37 or using the bio-potential plate 37 itself as the pick-up pad. It is also to be realized it is not necessary that the pick-up pad 51 actually contact the patient but that the present device 10 works through light clothing such as a T-shirt as a result of capacitive coupling between the bio-potential plate 37 or pick-up pad 51 and the bio-potential 50.

As also shown schematically in FIG. 2, an optional shunting resistor 113 is used to improve the stability of the DC bias shift and makes the device less prone to static electric fields caused by the environment and also by patient movement and build-up of static electricity charge. The resistor 113 varies in value depending on the bio-potential signal measured but typically falls in the 100 M$\Omega$ and 100 G$\Omega$ range.

As shown in FIGS. 1-3, a housing 80 surrounds the electro-optic device to seal it from the outside effects of electromagnetic (EM) fields and environmental changes, such as humidity that can effect the electro-optic material 31. As seen in FIGS. 2-3, unmodulated input light 22 is received by electro-optic modulator 30 from the light source 20 (FIG.

1) by means of input optical fiber 28 which is typically of the polarizing maintaining (PM) type which passes through housing 80. Similarly single mode (SM) type optical fiber 38 provides modulated light output 32 from modulator 30 and also passes through housing 80. Housing 80 is make of a non-electrically conducting material such as acrylonitrile-butadiene-styrene (ABS) plastic that is coated over on its exterior surfaces with a layer of conductive paint 81 (FIG. 3). Conductive layer 81 provides extra shielding from surrounding noise effects and provides an electrical ground return for the electro-optic modulator 30.

Figure 4:
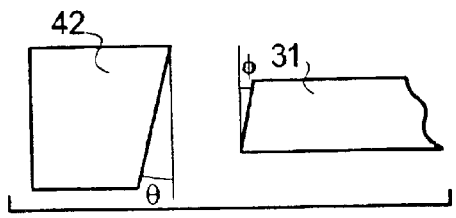
FIG. 4 is a partial side view of the end of the electro-optic modulator substrate and optical carrier illustrating angled mounting to reduce light reflection.

Fibers 28 and 38 are attached to the electro-optic modulator 30 by means of fiber-optic carriers 42 and 42', respectively (SDL Piri, Inc., Columbus, Ohio). The fiber-optic carriers 42, 42' are attached to crystal substrate 31 by using an ultra-violet curing or thermal adhesive 208. The fiber-optic carriers 42, 42' are typically small glass ferrules or machined glass blocks that are angle cut at an angle θ of 15.5 degrees to perpendicular and polished to minimize back-reflection from the substrate interface to the input and output fibers 28 and 38, respectively. Similarly and as shown in FIGS. 3 and 4, the crystal substrate 31 is also angle cut at an angle φ equal to about 10 degrees from perpendicular.

Figure 5:
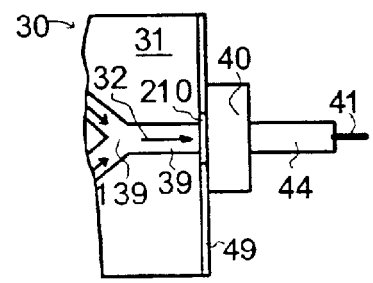
FIG. 5 is a partial view of the electro-optic modulator illustrating a spatial filter when mounting the receiver directly to the modulator substrate.
Figure 6:
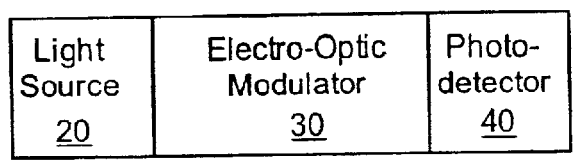
FIG. 6. Is a side view of an integrated light source, electro-optic modulator and photodetector assembly in which the light source and photodetector are mounted directly to the electro-optic modulator.

As shown in FIG. 6, it is possible to eliminate optical fibers 28 and 38 completely by attaching the light source 20 and the photodetector 40 directly to the electro-optic modulator 30 to form an integrated assembly that is placed in an appropriate housing 80 similar to the one described above with respect to FIGS. 1-3. A suitable light source 20 is the vertical cavity surface-emitting laser (VCSEL; Applied Optoelectronics, Inc.) which can be attached to the end of substrate 31 and provide light 22 directly to input waveguide 33. Similarly photodetector 40 is an indium gallium arsenide (InGaAs) photodiode of the ceramic submount type (FD150S3; Fermionics, Simi Valley, Calif.). As shown in FIG. 5, when the photodetector 40 is attached to substrate 31, the end of substrate 31 is covered with an opaque material 49 such as gold in which a small aperture 210 about 10 μm in diameter is formed and though which modulated light 32 flows to photodetector 40. The spatial filter arrangement of opaque end-covering material 49 and aperture 210 prevents excess light in substrate 31 from passing to photodetector 40. As with the attachment of the optical carrier 42' to the substrate 31, the end of substrate 31 is cut at an angle φ of about 10 degrees to perpendicular. The photodetector is titled at an angle θ of about 15 degrees and glued to the crystal substrate 31. This angular orientation, similar to that shown in FIG. 4, minimizes optical reflection back into waveguide 39. The electrical output 41 from photodetector 40 is shielded in a grounded, ultra-thin, coaxial cable 44 (1 mm in diameter). The total integrated package shown in FIG. 6 is contained in a housing 1.5 cm×0.75 cm×0.5 cm.

Figure 7:
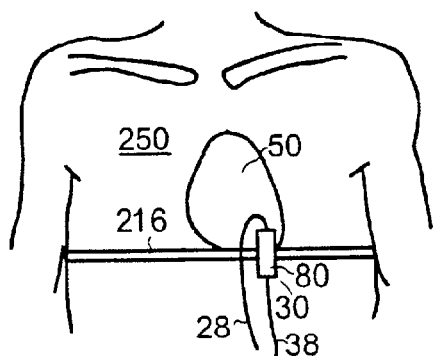
FIG. 7 is a front view of a partial torso of a patient showing the placement of a double optical fiber, high-impedance optical electrode held in position for taking an ECG with an elastic strap.
Figure 8:
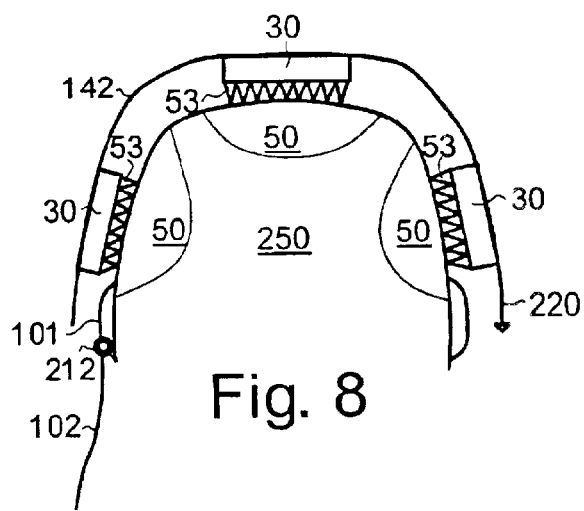
FIG. 8 is a front view of the location of the pilot tone attached to the ear of a patient and high-impedance electrodes with sensor pads mounted in a helmet for quick and easy positioning and also showing the saw-toothed pick-up pad for obtaining the bio-potential in hair covered areas of the body.

For ECG measurements and as shown in FIG. 7, the electro-optic modulator 30 is placed in proximity with bio-potential 50 and held in placed with an elastic band 216. For EEG measurements and as shown in FIG. 8, the requisite number of electro-optic modulators 30 can be incorporated into a cap or helmet 142 that brings the modulators 30 in the requisite proximity of the bio-potentials 50 of patient 250.

Electronic Circuitry

Except for the electronic processing required to eliminate noise and otherwise handle various electronic effects produced by the use of optical components, e.g., the light source and splitting of light into multiple paths to provide for multiple electro-optic modulators, i.e., bio-potential sensors 30, the electronic circuitry 60 for the signal processing of electronic signal 41 are conventional and are covered in standard handbooks and texts, e.g., *Medical Instrumentation, Application and Design,* 3rd edition, John G. Webster, editor; 1998 John Wiley & Sons, Inc, New York. The electronic circuitry 60 for processing output signal 41 to obtain the appropriate bio-potential output signal 62 comprises conventional filters, amplifiers, analog to digital converters, DC transient suppression circuits, and so forth and includes finding the correct voltage and frequency range of the signal to be processed. As seen in FIG. 9, after photodetector 40 converts modulated light 32 into electrical output 41, it is sent to post photodetector processing 160 where the signal is amplified and processed to provide linear output 45. Linear output 45 is then sent to a DC transient suppression circuit 70 to suppress large quasi-DC artifacts. DC transient suppression 70 provides for the blocking of quasi DC fields and enables fast recovery time from large DC transients that may be superimposed on the photodetector signal input 41. These transients occur in the environment and must be suppressed or subtracted out of the signal in order for a clear signal to be obtained. Once the transients are suppressed, the output 72 is passed along to further amplification circuitry 60. Amplification is necessary in view of the fact that the signal being processed is of a very low voltage level. For example, when looking at an alpha wave where the voltage range is approximately 20–200 mV, the voltage needs to be amplified by a factor of 100,000 in order for an oscilloscope to successfully see the signal in a 2–20 V range. Such amplification is typically preformed with operational amplifiers that provide various gains (i.e. a gain of 50 increases a 10 mV signal to 0.5 V) as specified by their manufacturers. The amplified signal 161 is then passed on to filtering 120. Filtering 120 limits the frequency range to match the signal being detected and thus maximizes the signal to noise ratio. For an alpha brain wave, the frequency lies in the range of 8–13 Hz. Therefore once the EEG is measured and amplified and DC suppressed, filters would eliminate all of the frequencies below and above the 8–13 Hz range. The final output 62 represents the alpha wave with its true amplitude and frequency characteristics. Aside from showing the actual amplification and filtering techniques, many software programs perform post signal processing similar to that performed by electronic circuitry 60 which takes the EEG or other bio-potential signal data and performs the amplification and filtering. Off the shelf amplifiers and filters are also available for real time data measuring. Such systems include the BIOPAC MP100 system (Biopac Systems Inc. Santa Barbara, Calif.), and LabVIEW (National Instruments, Austin, Tex.).

Figure 10:
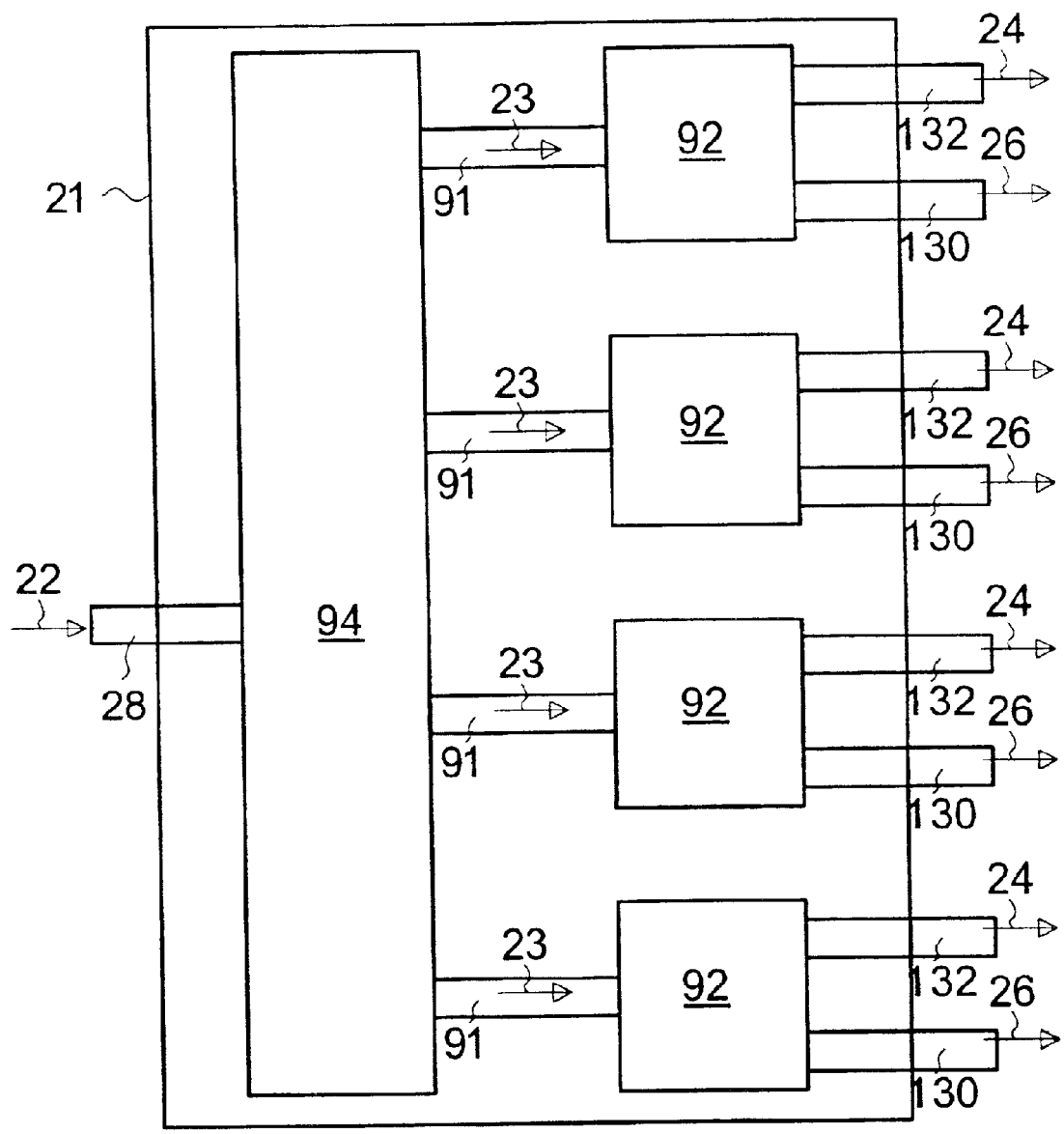
FIG. 10 is a schematic block diagram illustrating an optical splitter comprising an N-splitter and multiple X:Y splitters such as used to split a single light source into multiple channels with each channel further split into two channels, with one of the channels passing to the electro-optic modulator while the second passes to a reference photodetector. Such an arrangement is often used for a noisy light source.

FIG. 10 is another embodiment of the optical splitter 21 shown in FIG. 1 where the light source 20 sends unmodulated light 22 by means of PM input fiber 28 to optical power splitter 21. The optical power splitter 21 is comprised of an N-splitter 94 that divides the light along as many fibers 91 as there are electro-optic modulators 30. For example, the SM-1×8-M-PM/400 (SDL Piri, Inc., Columbus, Ohio) divides the power of the unmodulated light 22 to provide the same divided power of unmodulated light 22 along eight PM fibers 91, that is, if the power of unmodulated light 22 is 10 mW, each fiber 91 receives 1.25 mW of optical power. Although not illustrated, the power split unmodulated light 23 in PM fibers 91 can be sent directly to eight electro-optic modulators 30 as, for example, as required in a multiple channel EEG measurement where more than one electro-optic modulator 30 is used. An N-splitter 94 represents the simplest way of implementing a multiple channel system other than by using multiple light sources 20, that is, a separate light source 20 for each electro-optic modulator 30.

As used here, splitter 21 as shown in FIG. 1 is a generic term referring to a variety of splitters and combinations of splitters, e.g., N-splitter and X:Y splitters and their combinations which can be used to provide the requisite number of electro-optic modulators and reference light sources.

As seen in FIG. 10, the use of an X;Y splitter 92 provides a reference signal 26. As will be discussed below, reference signal 26 is sent to a reference photodetector 40r (FIG. 11). Optical splitter 21 is comprised of an N-splitter 94 and a X:Y splitter 92 for each channel provided by the N-splitter 94. The N-splitter 94 divides the power of the unmodulated light 22 into the requisite number of light fibers 23. N-splitter 94 sends light 23 along optic PM fiber 91 which is then attached to X:Y splitter 92. The X:Y splitter 92 divides light 23 and sends light 24 along PM fiber 132 to an electro-optic modulator 30 while the other PM fiber 130 sends light 26 directly to reference photodetector 40r.

Light 24 and 26 are both unmodulated; however, there is a difference in power of the light 26 that is sent to reference photodetector 40r. The X:Y splitter 92 is custom designed to provide a 2:1 power ratio between the reference photodiode 40r and signal photodiode 40. Because the electro-optic modulator 30 undergoes a total optical insertion loss, i.e. a power loss from the optical fibers, carriers, coupling, and in the substrate itself of about 6 dB, it is necessary to compensate for this loss by providing a 2:1 power ratio between the signal photodiode 40 and the reference photodiode 40r. As such, the X:Y splitter 92 must correspond to a 66:33 split, that is, a 66% power input to the modulator 30 and a 33% power input to the reference photodiode 40r. Thus the power input to modulator 30 is 0 dBm and the power input to the reference photodiode 40r is −3 dBm. The signal photodiode 40 sees a total power loss of −6 dBm while the reference photodiode 40r sees a power loss of −3 dBm thus giving rise to a 2:1 power ratio between the reference photodiode 40r and the signal photodiode 40.

Low-Coherent Laser Light Source

FIG. 11 gives the basic electronic circuitry 60 for a low-coherent (noisy) Fabry-Perot laser light source 20 (40 mW OKI laser diode DL3207N-40/CTM31) operating at a wavelength of 1.3 mm and having an optical isolator to mitigate the effects of optical feedback. The laser light source 20 is used for a single channel/single electro-optic modulator system with the light source 20 divided into two components by a two-channel splitter such as splitter 94 (FIG. 10) or 21 (FIG. 1) which delivers: 1) unmodulated light 24 to the electro-optic modulator 30 which in turn delivers modulated light 32 to signal photodetector 40 and 2) unmodulated light 26 to reference photodetector 40r. The laser diode light source 20 is operated and controlled with a laser diode power supply such as the ILX Lightwave (LDC-3722B).

Generally in selecting a laser driver light source 20, it is to be realized that drivers with excess noise characteristics in the lower frequencies of the laser current are best avoided. Low noise drivers, on the other hand, obviate the need to use super low noise receivers. The laser power supply should exhibit a low excess intensity noise across a very wide audio and radio frequency spectrum. Such intensity noise is commonly referred to a Relative Intensity Noise (RIN) and is equal to the inverse of the Carrier to Noise Ratio (CNR) normalized to a 1 Hz bandwidth. For a quantum-limited photodetector, the Carrier to Noise Ratio is defined by the following equation:

$$CNR = hP/2hfB \qquad (1)$$

where h is the quantum efficiency, P is the photodetector power, h is Planks constant, f is the optical frequency, and B is the detection Bandwidth in Hz. A typical RIN is on the order of −160 dBc for 10 mW of optical power, or −150 dBc for 1 mW of optical power.

Figure 12C:
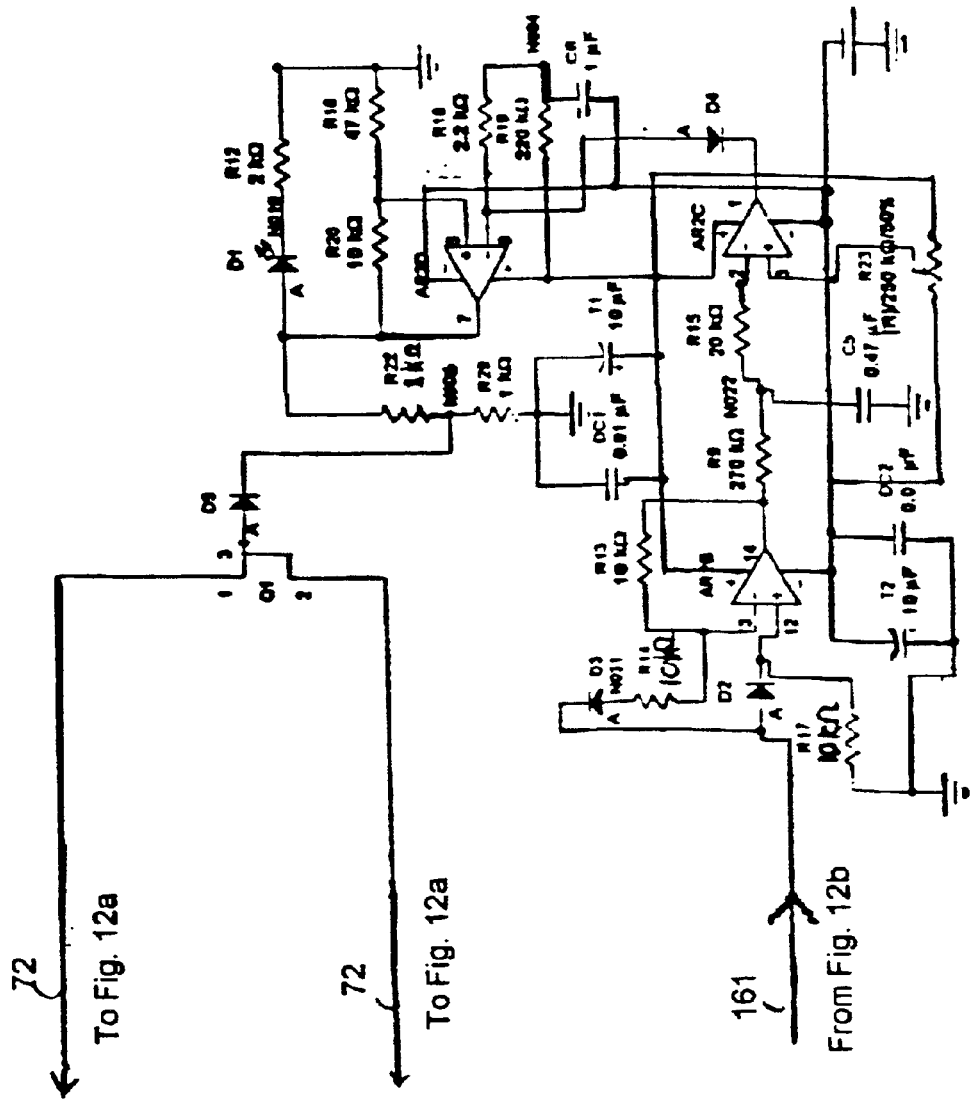
FIG. 12c is a detailed schematic of the DC transient suppression block shown in FIG. 11.
Figure 12D:
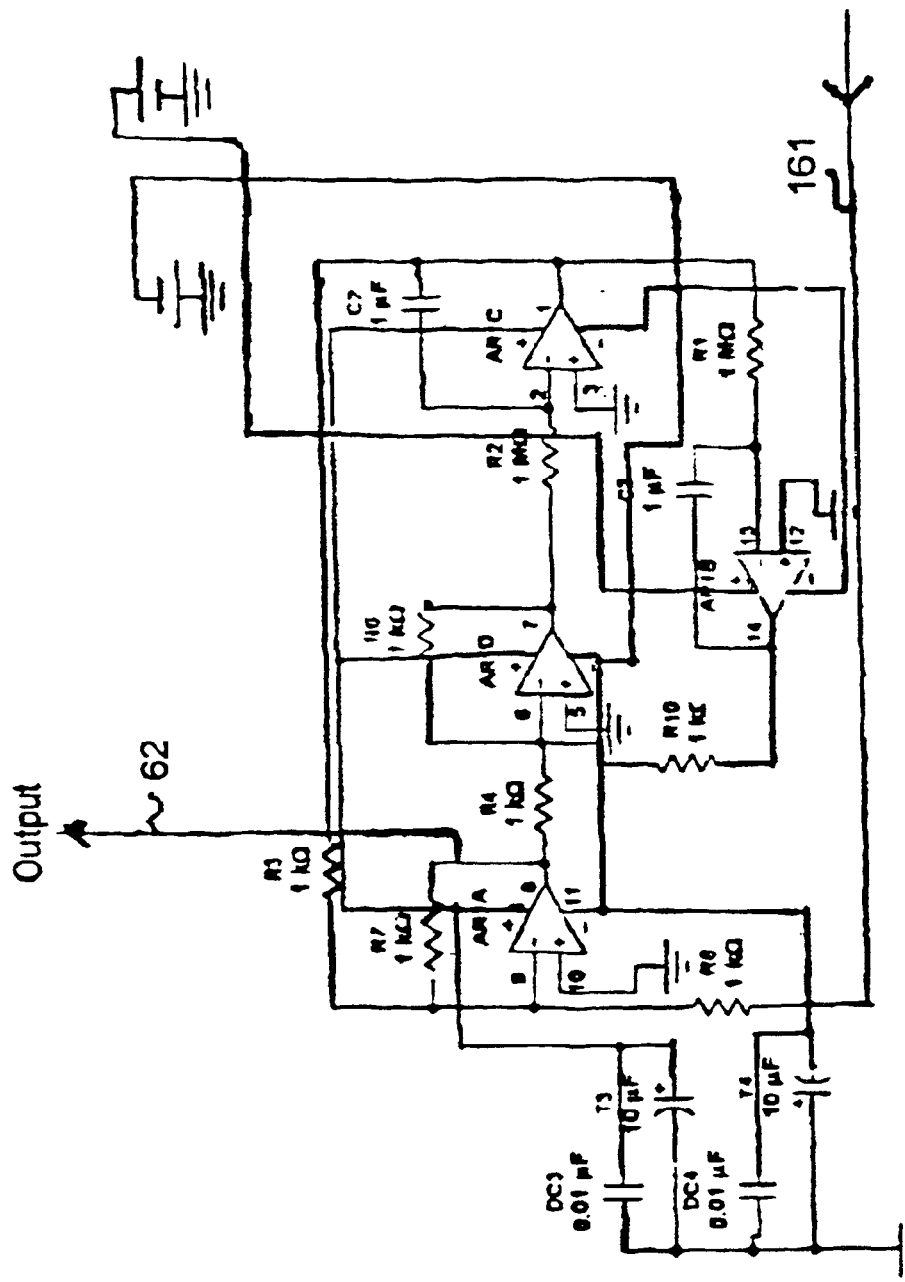
FIG. 12d is a detailed schematic of the filtering block shown in FIG. 11.

A Fabry-Perot laser typically has a RIN level of −130 dBc for 10 mW of optical power and thus is quite noisy with 30 dB of excess intensity noise. As such, a super low noise receiver is required in post photodetector processing 160 to eliminate the 30 dB of excess noise. FIG. 12a-d is a detailed diagram of the electronic circuitry 60 shown in FIG. 11 for the processing of a low-coherent laser light source 20 and consists of four parts: FIG. 12a details post photodetector processing 160, FIG. 12b shows amplification circuitry 60, FIG. 12c provides details of the DC transient suppression circuitry 70, and FIG. 12d gives the details of the filtering circuitry 120.

High-Coherent, Low Noise Laser Light Source

Figure 13:
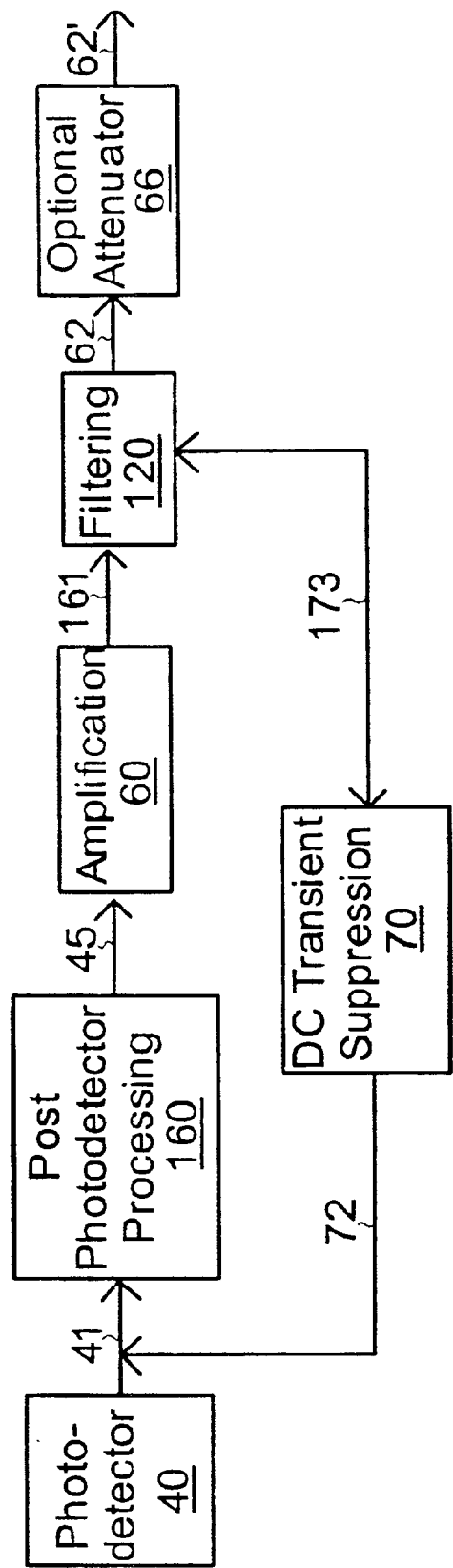
FIG. 13 is a schematic block diagram illustrating the arrangement of the major components of the electronic circuitry (signal photodetector, post-photodetector processing circuitry, DC transient suppression circuitry, amplification circuitry, filtering circuitry, and optional attenuator) when a highly-coherent, low noise laser light source is used.
Figure 14:
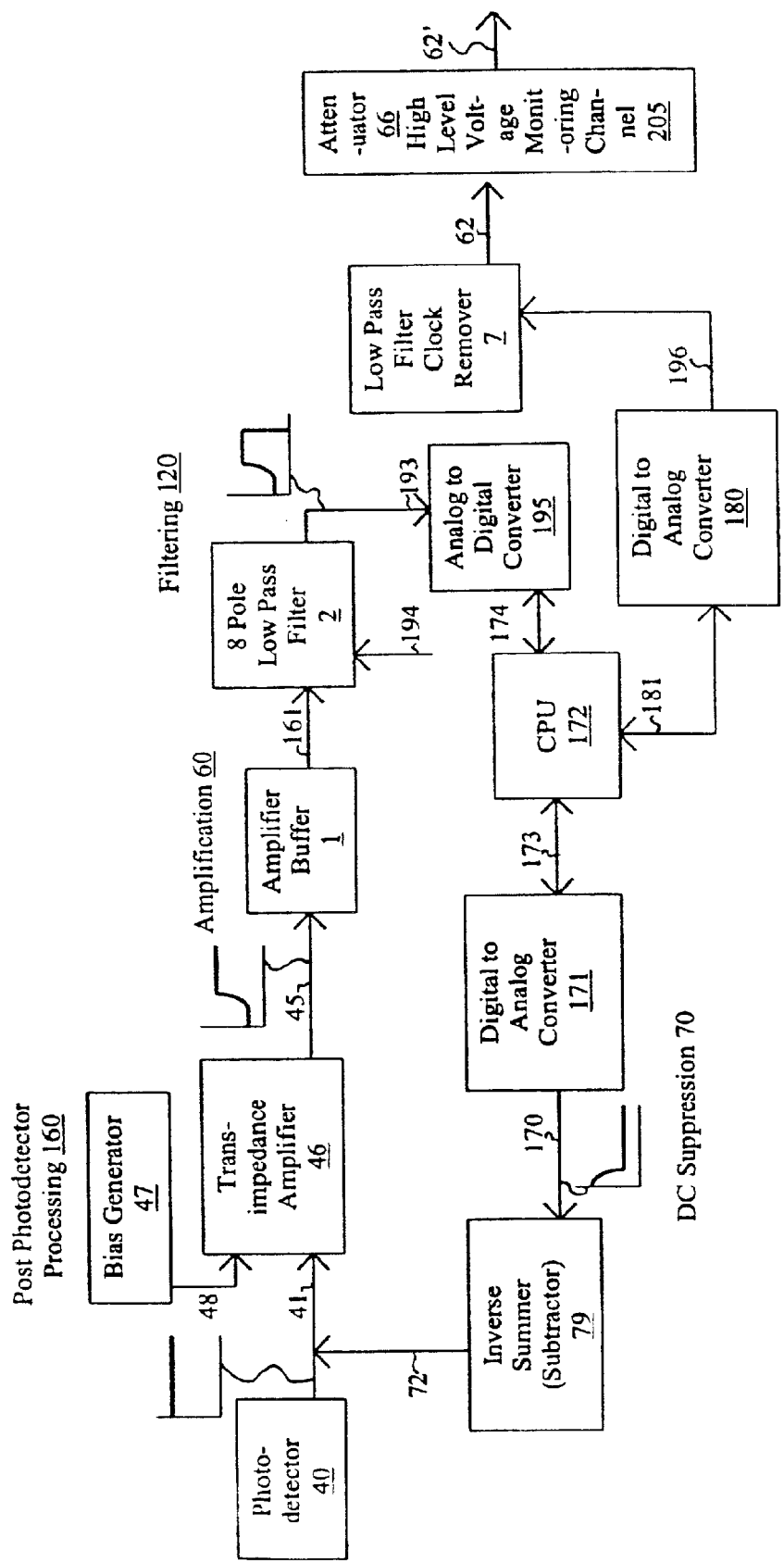
FIG. 14 is a schematic block diagram giving additional detail for FIG. 13 by showing major processing circuitry within each block of FIG. 13.

FIGS. 13-15f illustrate the electronic circuitry 60 used with a highly-coherent, low noise laser light source 20. Referring initially to FIGS. 13 and 14, photodetector 40 provides an electrical output 41 which is initially sent to post photodetector processing electronics 160. The post photodetector processing module 160 consists of a bias generator 47 and a trans-impedance amplifier 46. The electrical output 41 is connected to the inverting input on the trans-impedance amplifier 46. The bias generator 47 supplies a bias voltage 48 that is connected to the non-inverting terminal on the trans-impedance amplifier 46 to ensure that the photodetector 40 will be reversed biased for the photo-conductive mode of operation. The trans-impedance amplifier 46 produces a linear output 45 that is linear with respect to the input bio-potential 50. Output 45 is sent to amplification circuitry 60. Even though the trans-impedance amplifier 46 produces a linear output voltage 45, the true bio-potential signal is contaminated with noise from electronic components, the environment, and so forth and therefore further processing must take place. The amplification circuitry 60 comprises an amplifier buffer 1. Amplifier buffer 1 amplifies the linear voltage 45 to supply an output voltage 161 to filtering circuitry 120. Amplifier circuitry 60, for the purpose of reading an EEG signal, has a gain of 50. Such high gain is needed in order to bring voltage 45 up to a usable level for filtering and further signal processing to take place. Digital components are used for further signal processing and will not operate correctly when the voltage is at the mV level. As such, amplification is necessary in order for the digital components to work successfully as designed. The filtering circuitry 120 consists of an eight-pole low pass filter 2, analog to digital converter 195, central processing unit (CPU) 172, digital to analog converter 180, and low pass filter clock remover 7. The eight-pole low pass filter 2, which is also referred to as an eight order filter (MAX296, Maxim Integrated Products, Sunnyvale, Calif.), is a digital component requiring a clock frequency 194 in order to operate correctly. The eight-pole low pass filter 2 is of the eight pole Bessel type in order to provide a steep characteristic response, i.e. low overshoot and fast settling time, to signal 161. In addition, the eight-pole low pass filter 2 is of the digital filter type achieving better performance than standard analog filters. The eight-pole low pass filter provides a filtered analog output 193. For EEG processing, the cutoff frequency is set at 380 Hz to include the bio-potential signal frequency and a pilot tone frequency which will be discussed further below. The filtered analog output 193 is sent to a analog to digital (A/D) converter 195 (WinSystems PCM A/D-16, WinSystems Inc., Arlington, Tex.) that converts the analog signal 193 to a digital signal 174. The A/D converter 195 samples the filtered analog signal 193 and processes it into digital bits. This digital information 174 is then sent to the Central Processing Unit (CPU) 172. The CPU 172 (WinSystems PCM-586 board, WinSystems Inc.), is a single-board computer. The CPU 172 handshakes (exchanges information) with the A/D converter 195. This handshaking allows for the fast transfer of data from the input and output terminals of the CPU 172 with the A/D converter 195. Similarly the CPU 172 handshakes with two Digital to Analog Converters 180 and 171 (WinSystems PCM-D/A12, WinSystems Inc.) by means of connections 181 and 173, respectively. The CPU is programmed to function as a filter which for the EEG case, passes frequencies that typically lie in the 1–100 Hz range.

The dynamic range of the bio-potential signal of interest is small compared to DC and low frequency offsets for a variety of reasons including motion of the optical fibers and/or the modulator itself, variations in optical input power, drift of component characteristics with time and/or temperature, and so forth. These "quasi-DC" (QDC) offsets must be removed (nulled) at the trans-impedance amplifier to avoid saturating amplifier 1 and filter 2 components. This nulling or "QDC removal" function is implemented as a periodic correction made at a preprogrammed time interval. In the current embodiment, this interval is 0.5 seconds.

The CPU 172 is programmed to monitor the sampled value of the amplified and filtered analog signal 193 as sampled and converted by the A/D converter 195. A sliding average of the sampled value is calculated over the preprogrammed time interval and is compared with two preprogrammed threshold values of equal absolute value and opposite sign. These threshold values are calculated to be at a level such that if the sliding average exceeds (in absolute value) either threshold, it provides a reliable indication that saturation is imminent.

The CPU 172 is programmed to react to either threshold being exceeded by incrementing or decrementing, as appropriate, digital signal 173. Another D/A converter 171 and inverse summer (subtraction) 79 function together as the DC suppression circuit 70. D/A converter 171 converts this digital signal to analog signal 170, which is applied as a control voltage to inverse summer (subtraction) 79. This control voltage is converted to a current 72 that is subtracted from the photodetector output current 41.

Figure 15A:
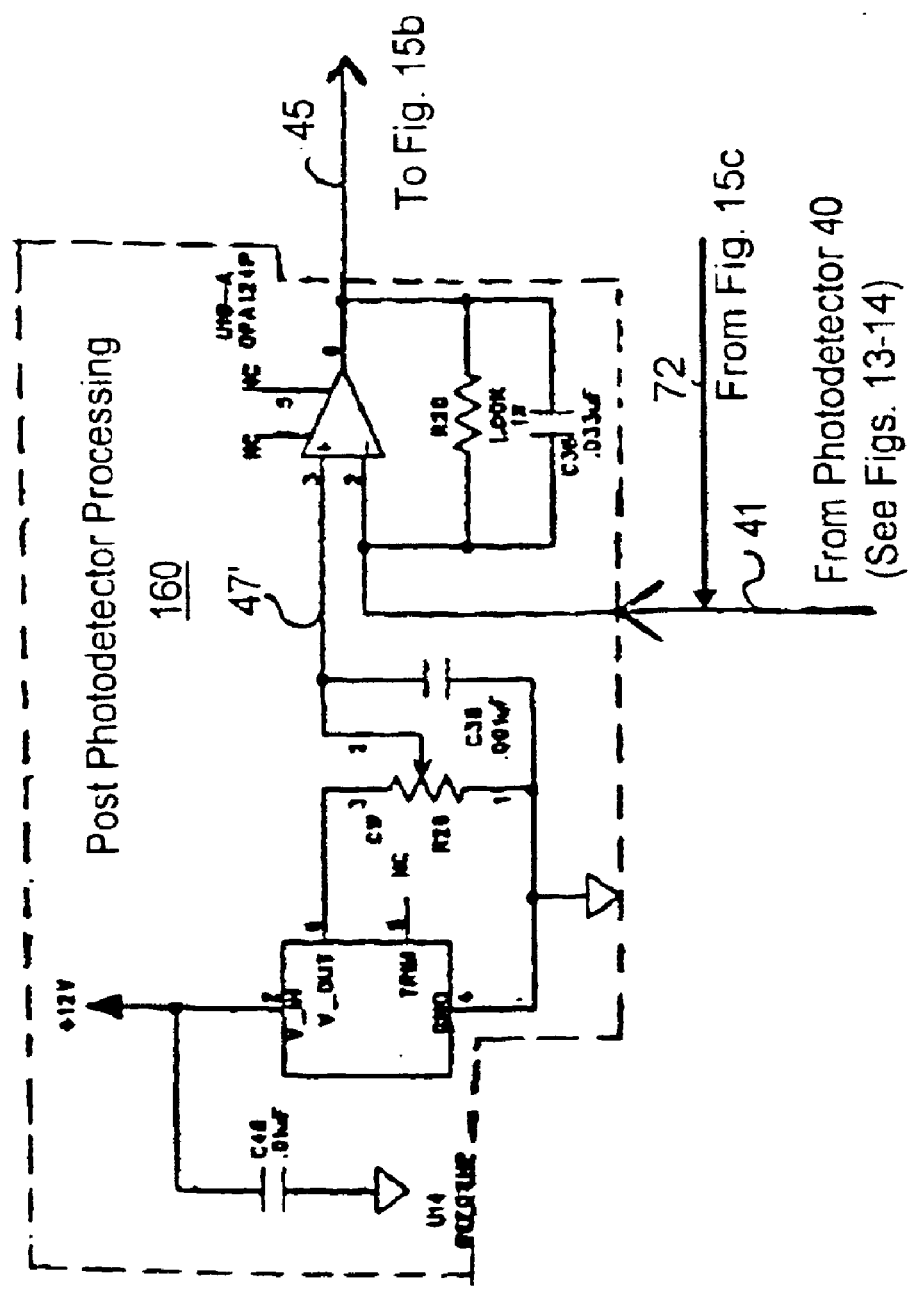
FIG. 15a is a detailed schematic of the post-photodetector processing block shown in FIGS. 13 and 14.
Figure 15B:
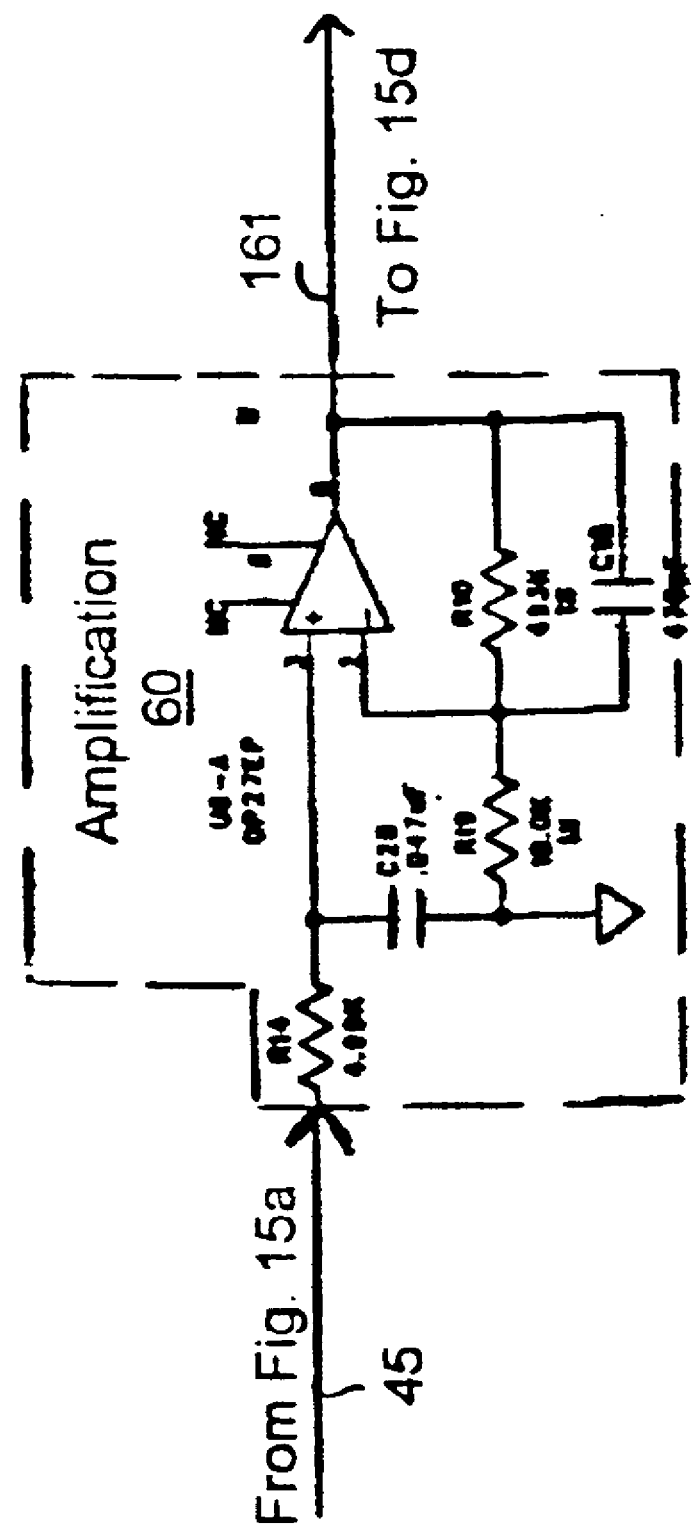
FIG. 15b is a detailed schematic of the amplification processing block shown in FIGS. 13 and 14.
Figure 15E:
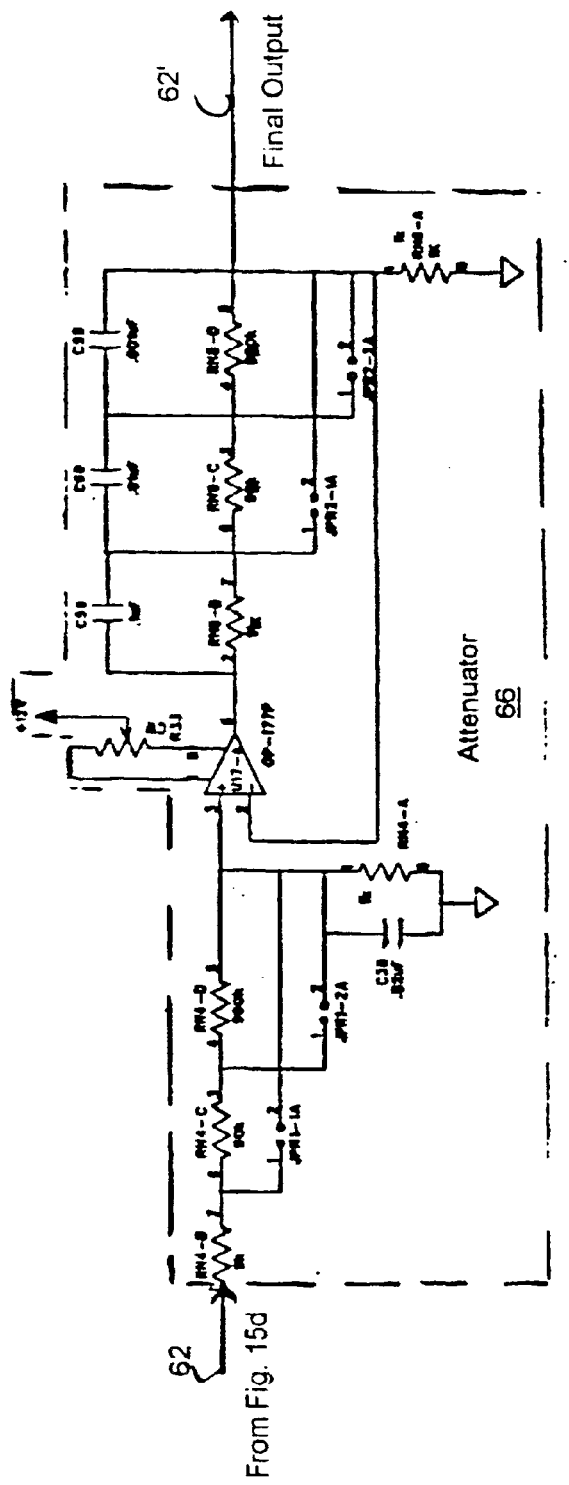
FIG. 15e is a detailed schematic of the attenuator circuit block shown in FIGS. 13 and 14.
Figure 15F:
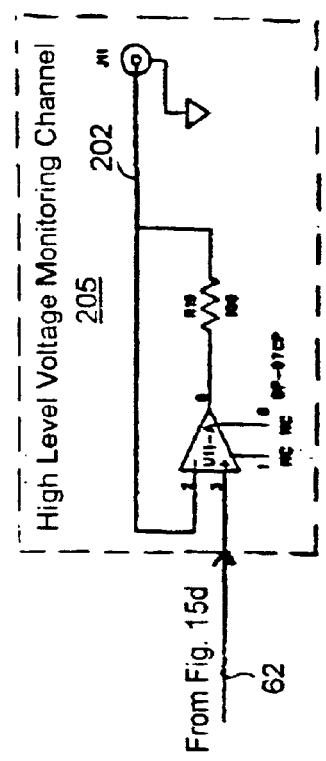
FIG. 15f is a detailed schematic of the high level voltage monitoring channel block shown in FIG. 14.

Once the CPU 172 obtains the true bio-potential signal in digital form it sends the information to the D/A converter 180 via 181. The D/A converter 180 then converts the digital signal 181 back to analog form 196 which is then sent to low pass filter clock remover 7 which removes the clock frequency 194 that controlled the eight-pole low pass filter 2. Removal of the clock frequency 194 provides the final bio-potential output signal 62. An attenuator 66 and/or a high voltage level monitoring channel 205 (i.e. oscilloscope, FIG. 15e) can also be used for EEG signal monitoring. Since the output signal 62 is much higher than the EEG signal due to the high amplification, it can be sent directly to an instrument such as an oscilloscope to measure the high level voltage signal. As seen in FIG. 15f, high level voltage monitoring channel 205 provides signal 202 which can be used directly with an oscilloscope for measuring the high level voltage signal. On the other hand, if the user wishes to use conventional high sensitivity EEG recording instruments, output signal 62 is sent to an attenuator 66 in order to return the voltage back to its original value prior to sending the signal to conventional high sensitivity EEG recording instruments.

FIGS. 15a-f illustrate the details of the electronic circuitry 60 used with a high coherent low noise laser light input 20 and include the inputs, outputs and components associated with post photodetector processing (FIG. 15a), amplification (FIG. 15b), DC transient suppression (FIG. 15c), filtering (FIG. 15d), signal attenuation (FIG. 15e) and provision of a high level voltage monitoring channel (FIG. 15f).

Pilot Tone Signal

Figure 16:
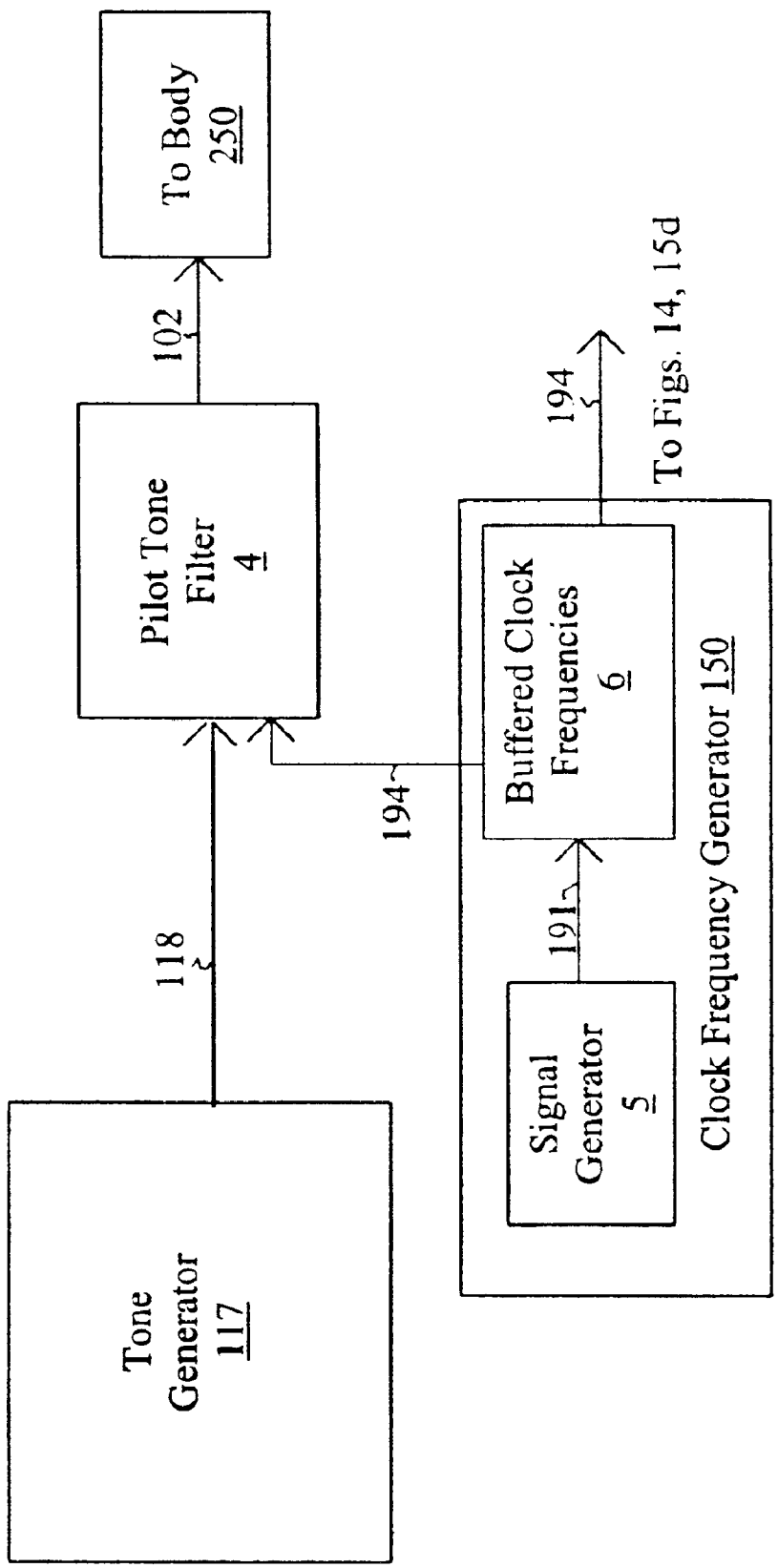
FIG. 16 is a block diagram that illustrates the circuitry associated with adjusting the sensitivities of multiple optical modulators 30.
Figure 17A:
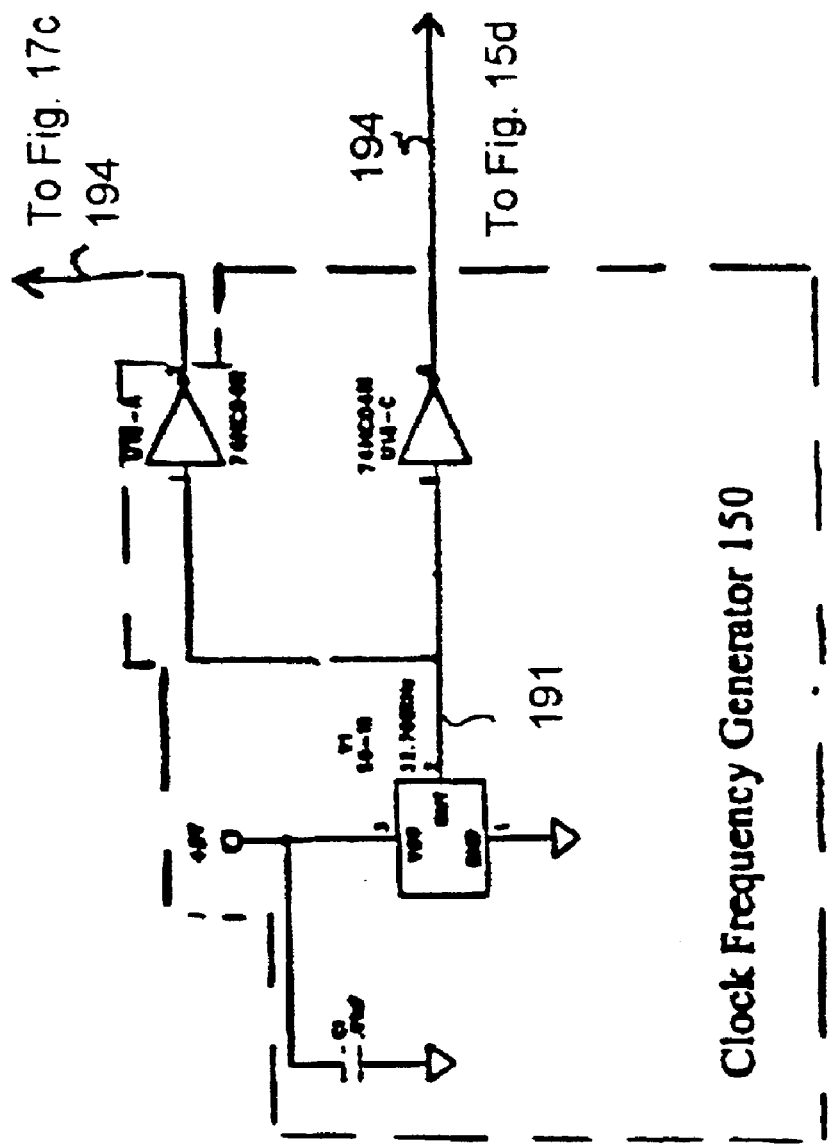
FIG. 17a is a detailed schematic of the clock frequency generator shown in FIG. 16.
Figure 17B:
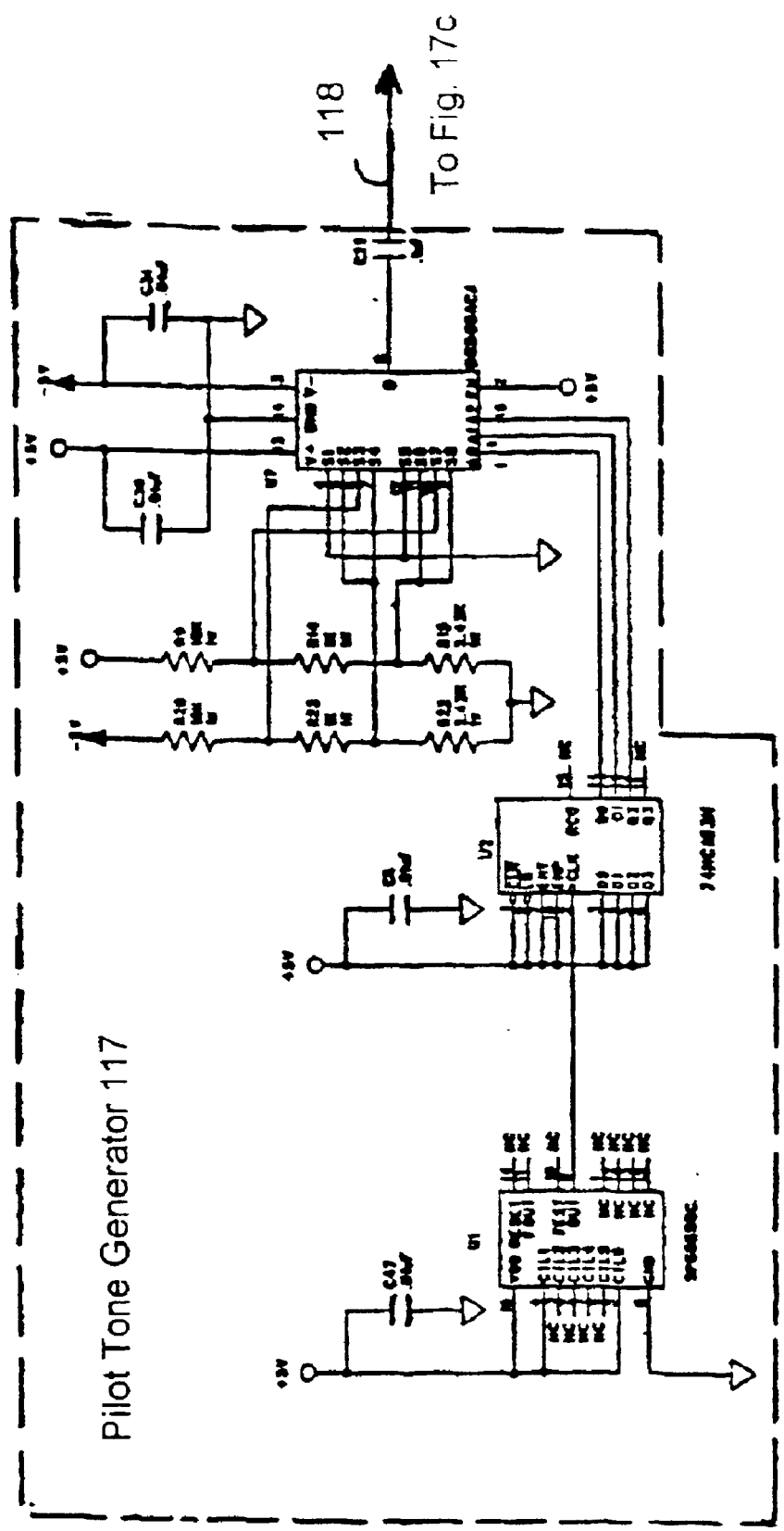
FIG. 17b is a detailed schematic of the pilot tone generator shown in FIG. 16.
Figure 17C:
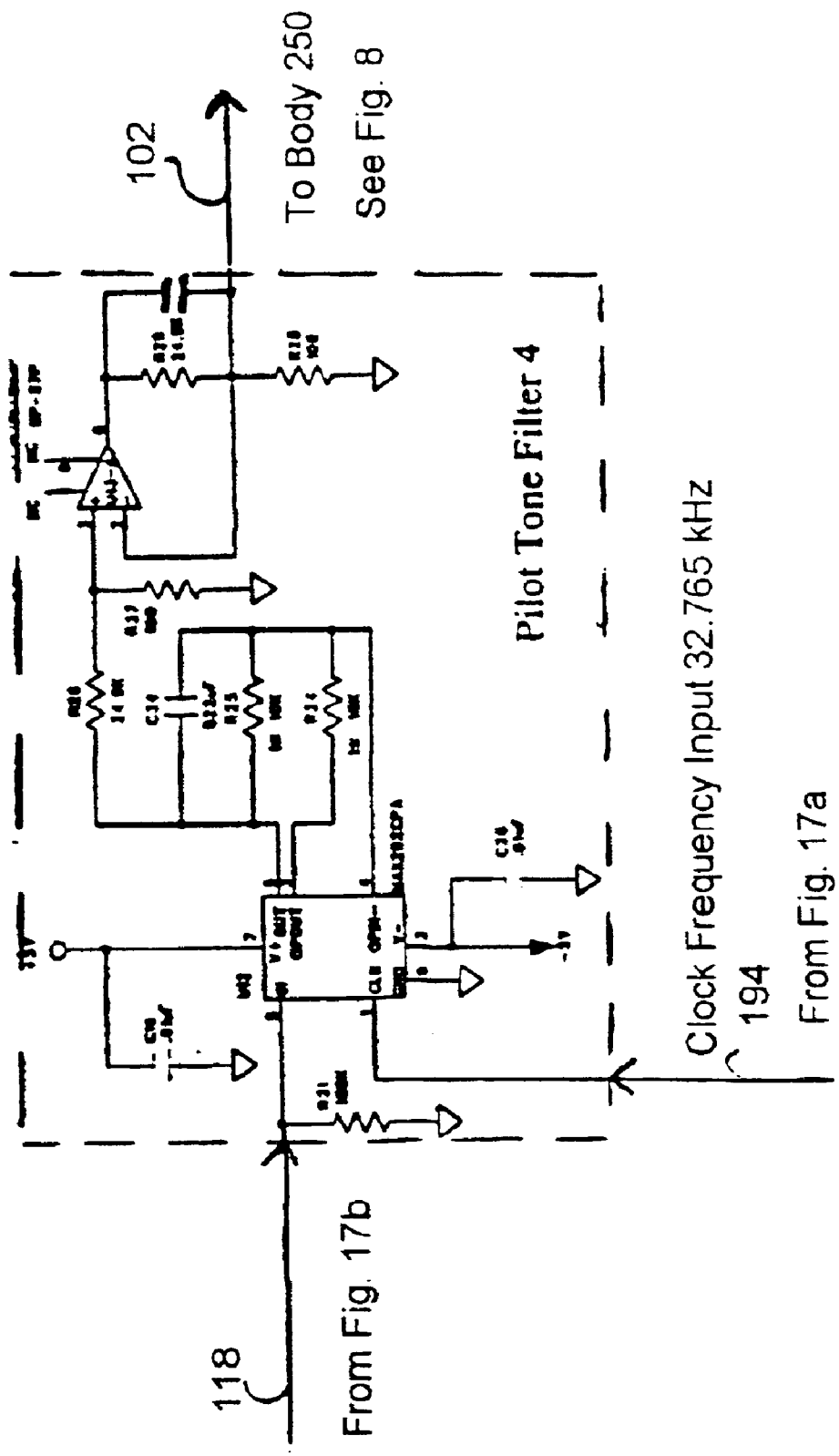
FIG. 17c is a detailed schematic of the pilot tone filter shown in FIG. 16.

FIGS. 16-17c illustrates the circuitry involved in adjusting the sensitivities of multiple optical modulators 30. A tone generator 117 creates a pilot tone signal 118 that is filtered by filtering circuit 4 to produce a reference signal frequency 102 that is above the frequency being measured, i.e., typically around 300 Hz. A clock frequency generator 150 comprises a signal generator 5 that produces a signal 191 which is sent into a buffer 6 that controls the output clock frequency signal 194. The buffer 6 ensures that signal 194 is produced correctly and without any interference. The clock frequency of signal 194 is 32.76 kHz and provides operational status to the pilot tone filter 4, a digital component, and also to the filtering circuit 120 of FIGS. 13, 14, 15d. The filtered pilot output tone 102 is sent to the patient 250 (FIG. 8) by, for example, attaching the pilot tone 102 to ear 101 by means of an ear clip 212. The 300 Hz tone is applied to the patient 250 as a common-mode signal for all the optical modulators 30 in use and is used to modulate respective automatic gain control (AGC) circuits for each electro-optic device 30. This signal is superimposed on each electro-optic device 30 as shown in FIG. 8.

To achieve AGC, the CPU 172 of FIGS. 14, 15d stores the known frequency and amplitude of the pilot tone 102, that is, stores a 300 Hz tone amplitude of 0.05 mV). The pilot tone signal 102 superimposes itself on each modulator 30 and is passed to the CPU 172 which is programmed to bandpass the pilot tone signal 102 with a start cutoff frequency at 301 Hz and an end cutoff frequency at 302 Hz. The eight pole low pass filter 2 (FIGS. 14, 15d) is not a problem as it was designed to pass frequencies below 380 Hz. The CPU 172 compares the unknown pilot tone signal amplitude with the known pilot tone signal amplitude. If the two do not match, a correction is applied, that is, if CPU 172 receives a signal of 0.03 mV and compares it to 0.05 mV, an amplitude correction of 0.02 mV is applied and passed on to the D/A converters. This circuitry is a way of aligning multiple electro-optic devices 30 to be identical and constant with respect to their sensitivities and it also provides a unique calibration protocol that ensures that the modulators 30 are in alignment. The current design call for a cycling of the protocol once every 0.5 seconds. The pilot tone signal 102 provides the means of measuring and stabilizing the gain (sensitivity) of the electro-optic modulator 30 with respect to the changes in the detected optical power (not due to the bio-potential signal 50) and/or any drastic changes in the contact resistance (due to the bio-potential 50).

FIGS. 17a-c provide the details of the circuitry used for the pilot tone device used to maintain equal sensitivity for multiple electro-optic modulators 30. FIG. 17a provides the details of the clock frequency generator 150; FIG. 17b provides details of the pilot tone generator 117; and FIG. 17c gives the details of the pilot tone filter 4. FIG. 8 shows the pilot tone 102 superimposed on several electro-optic modulators 30. The modulators 30 are enclosed in helmet 142 where a universal ground is established that is shared by all of the modulators 30.

Phase-Modulation

Figure 19:
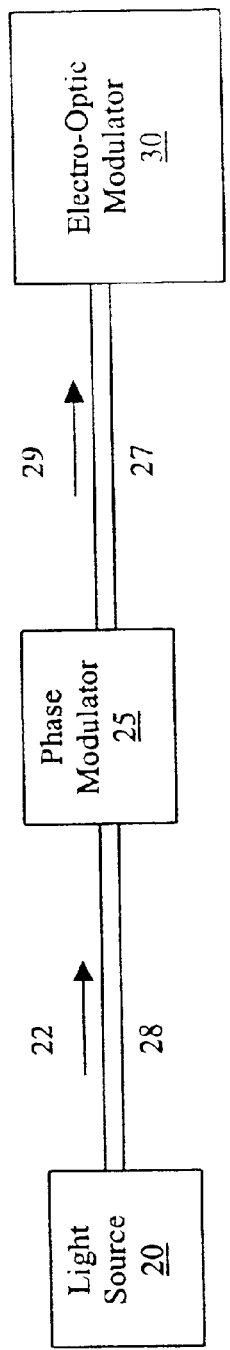
FIG. 19 is a block diagram that illustrates the positioning of a phase modulator between the light source and electro-optical modulator.
Figure 20:
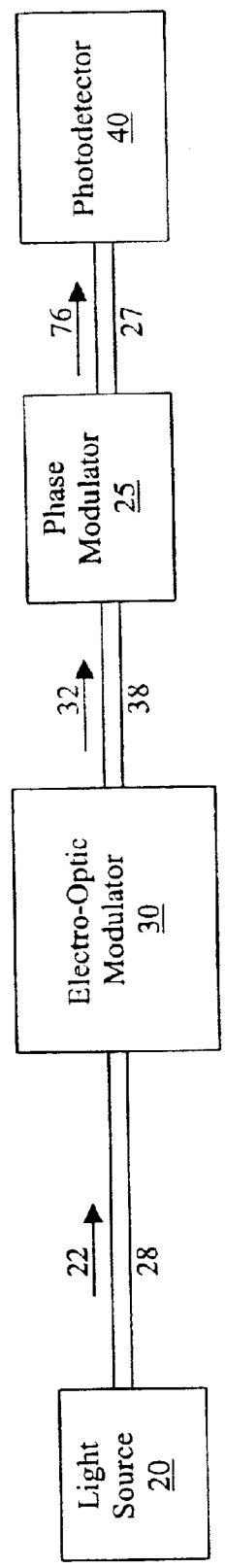
FIG. 20 is a block diagram that illustrates the position of a phase modulator between the electro-optic modulator and the photo-detector.
Figure 21:
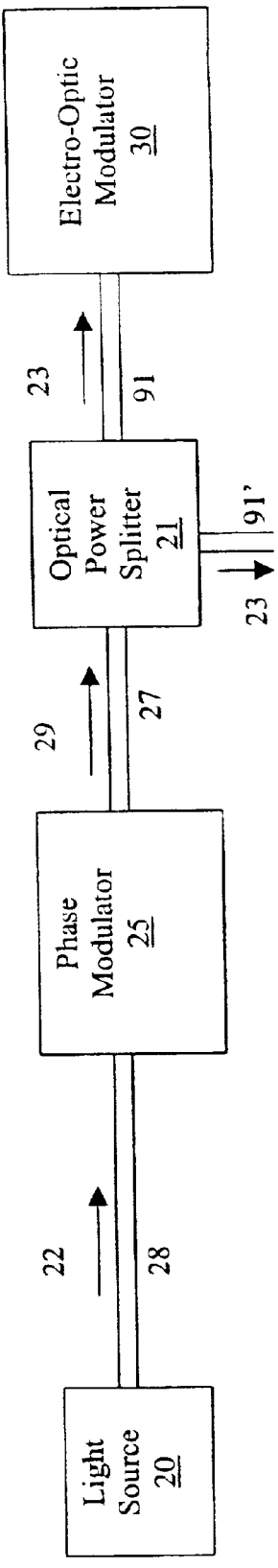
FIG. 21 is a block diagram that illustrates the use of a phase modulator and an optical power splitter between the light source and electro-optic modulator.

FIGS. 18-27 present additional features of the invention that provide for the elimination of noise in the measured bio-potential as a result of the optical technique used to obtain the bio-potential 50 and is especially useful when several electro-optic devices 30 are used to measure biopotentials. Typically the light source 20 is a high-coherent Ortel DFB (distributed feedback) laser (Ortel Corporation part of Lucent Technologies Microelectronics Group, Alhambra, Calif.) used with an InGaAs photodiode photodetector 40. The Ortel 40 mW DFB laser operates at 1550 nm and includes an optical isolator to prevent optical feedback into the laser cavity causing intensity and frequency disturbances. The laser light source 20 uses a 250 mA Thors Lab LD1100 laser driver with 0.1 mA root-mean-square noise. The light source 20 is connected to the electro-optic modulator 30 by means of a PM input fiber 28. Since a DFB laser intensity type is providing typical RIN values close to the quantum limit (−150 dBc to −160 dBc), a super low noise receiver as noted above with respect to the discussion of FIG. 11 is not needed. However, highly coherent DFB lasers produce interferometric noise which is also termed coherent back reflection noise or 1/f noise. This back reflection noise is due to the optical reflections propagating back and forth between the laser light source 20 and photodetector 40 along the optical fibers. In mathematical terms the back reflection is expressed as a Bessel function where:

$$\text{Interferometric Noise} = J_0(2Df \sin[2pf_m t]) \quad (2)$$

where $J_0$ is the Bessel function of zero-order, Df is the phase deviation (radians), $f_m$ is the modulation frequency imposed on a phase modulator 25, and is the round-trip delay time. The back reflection is created by the highly coherent light 22 going through the electro-optic device once accounting for a $Df_n$ (n=noise) phase deviation. Once the light 32 is received by the photodetector 40 it is reflected back into the electro-optic modulator 30 to the light source 20 thereby picking up another $Df_n$, thus totaling $2Df_n$, which then gets reflected back into the electro-optic modulator 30 picking up another $Df_n$, thus totaling $3Df_n$ (FIG. 18). In order to address the issue of back reflection noise, the present invention employs ways to deal with the noise directly. Back reflection noise in fiber optics can be substantially reduced in a variety of ways, such as by using a PZT (lead zirconate titanate) piezo-electric ceramic, around which can be directly wrapped the optical fiber 28, like a coil, thereby producing a phase modulation in the light 22 that resides inside the fiber 28. Another way to reduce back reflection noise is to apply a direct high frequency tone to the light source 20 thereby imposing a phase modulation directly to the light source 20. In this case the DFB laser type would have a second coupled cavity by which a phase modulation would be applied. Currently this method involves expensive lasers available in the field of fiber optics. Another direct method is to modulate the current flow or temperature of the laser to induce a chirp, (frequency change) that would thereby change the frequency of the laser. This could be done with fast electronic tunable lasers that are able to produce a frequency (chirp) rapidly. However, this technology is also not available at low cost. Therefore, in the present invention the most practical and employed way to reduce the back reflection noise is by applying an electro-optic phase modulator 25 between the light source 20 and the photodetector 40. FIGS. 19-21 show three different ways of doing this. The first method (FIG. 19) employs a phase modulator 25 placed between the light source 20 and the electro optic device 30. The phase modulator 25 produces a phase modulated unmodulated intensity light 29, which is sent down another optical fiber 27, preferably of the PM type. The second method (FIG. 20) shows the phase modulator 25 placed between the electro-optic device 30 and the photodetector 40. In this method, the electro-optic device 30 produces an intensity modulated output 32 that is passed along optical fiber 38 to the phase modulator 25 which sends the phase and intensity modulated light 76 down another optical fiber 27, preferably of the SM type, to the photodetector 40. Both of these methods (FIGS. 19 and 20) work best with a one-channel system operating with a DFB laser type as the light source 20. The third method (FIG. 21) shows the phase modulator 25 and an optical power splitter 21 between the electro-optic device 30 and light source 20. The unmodulated light 22 is sent into the phase modulator 25 by means of fiber 28. The phase modulator 25 then sends phase modulated light 29 into the optical power splitter 21 by means of optical fiber 27, typically of the PM type. In this case, the power splitter 21 then sends the power split intensity modulated light 23 to optical fiber 91 which is then connected to the electro-optic device 30. The intensity modulated power split light 23 is also sent to multiple optical fibers 91 which can be used to connect to other electro-optic devices 30. Also, this method would show the phase modulator 25 between the electro-optic device 30 and the photodetector 40, much like FIG. 20. In FIG. 21, the power splitter 21 is located between the light source 20 and electro-optic device 30. However, it is noted that in the present invention this technique was not favorable to stopping the noise imposed on the power splitter 21 by the light source 20 which would then be carried to other electro-optic devices 30 via 91. In the present invention, the third and final method is employed for using a phase modulator 25 for a multiple channel system with a DFB laser type. FIG. 22 shows the net phase modulation when the phase modulator is implemented between the electro-optic device 30 and the light source 20.

Figure 23:
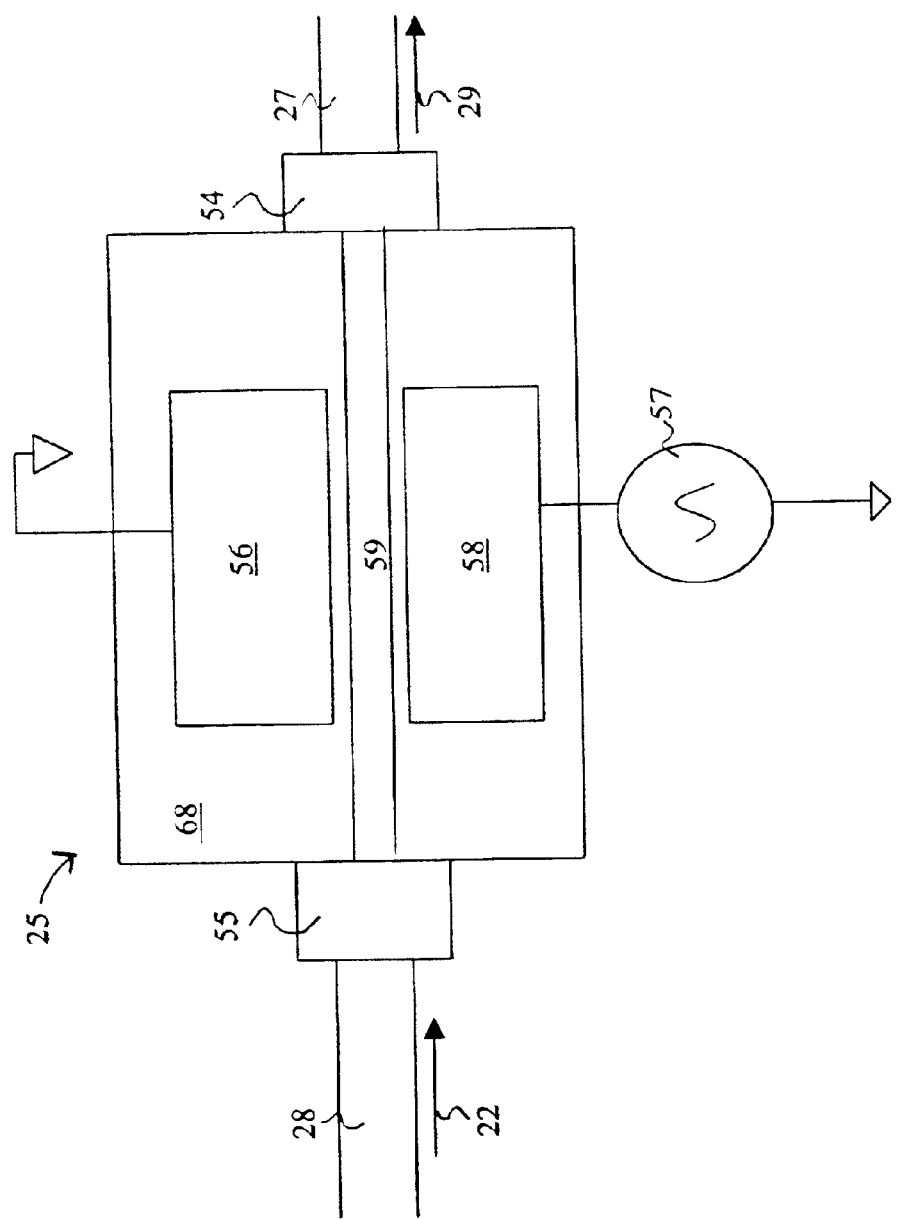
FIG. 23 is a top view of a phase modulator illustrating the waveguide, electrodes, and light source and electro-optic modulator optical fiber connections to the phase modulator.

FIG. 23 shows the phase modulator 25 in a detailed schematic diagram in relation to the method shown in FIG. 21. The unmodulated light 22 flows down the PM fiber 28, which is attached directly to the phase modulator waveguide 59 by means of carrier 55. Typically carriers 55 and 54 are glued to the substrate 68 in a fashion similar to that by which optical fibers are attached to the Mach-Zehnder device shown in FIGS. 3 and 4. The phase modulator waveguide 59 is typically about 20 mm in length and 7 mm in width and formed in a lithium niobate crystal substrate 68 that is 20 mm long and 5 mm wide. The waveguide 59 receives an induced field by means of a signal generator 57, typically an AC signal source, which is electrically connected to electrode 58 while electrode 56 is referenced to ground. The electrodes 56 and 58 are 10 mm long by 25 mm wide and placed in close proximity (each about 5 mm from the waveguide 59) so that a strong field is induced. The signal generator 57 is set to produce a frequency higher than that of the signal being measured. Therefore if measuring an EEG, the frequency would be outside the range of 100 Hz, thus a 10 kHz frequency would be used to drive the excess back reflection noise outside the range of the bio-potential signal and would then be driven to the frequency imposed on the fiber by the modulator (further discussed with respect to FIGS. 24(a)-(d)). The induced field causes the unmodulated light in the waveguide 59 to become a phase modulated light output 29, thus the energy is dispersed from the low frequency to the high frequency induced above and outside the spectrum of interest on the unmodulated light 22. Carrier 54 connects the waveguide 59 and PM optical fiber 27. The PM optical fiber 27 is then sent to the electro-optic modulator device 30.

Figure 24A:
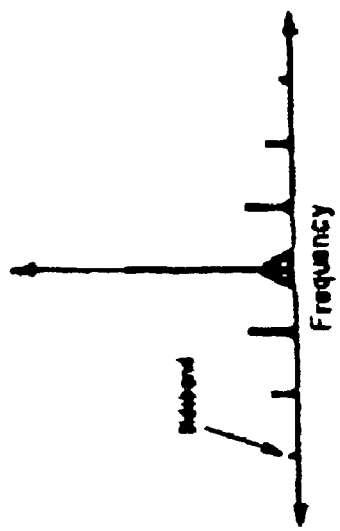
FIGS. 24(a), 24(b), 24(c), and 24(d) show the noise dispersion when various degrees of phase modulation are applied to the light in the optic electrode system.
Figure 24B:
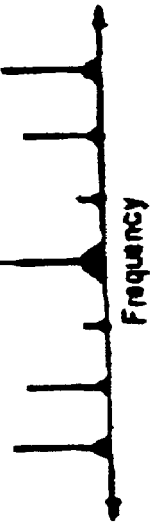
Figure 24C:
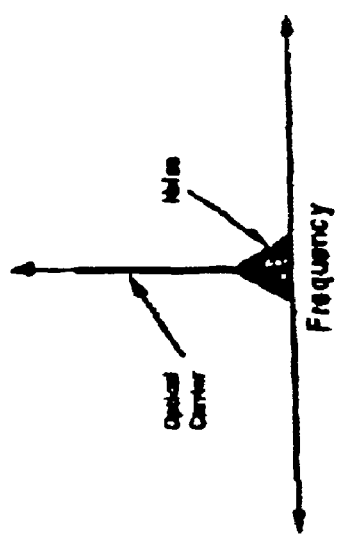
Figure 24D:
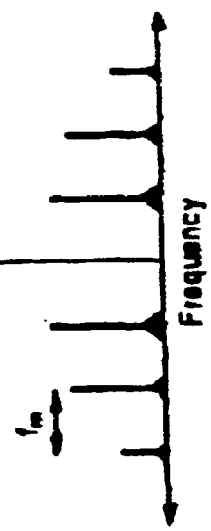
Figure 26:
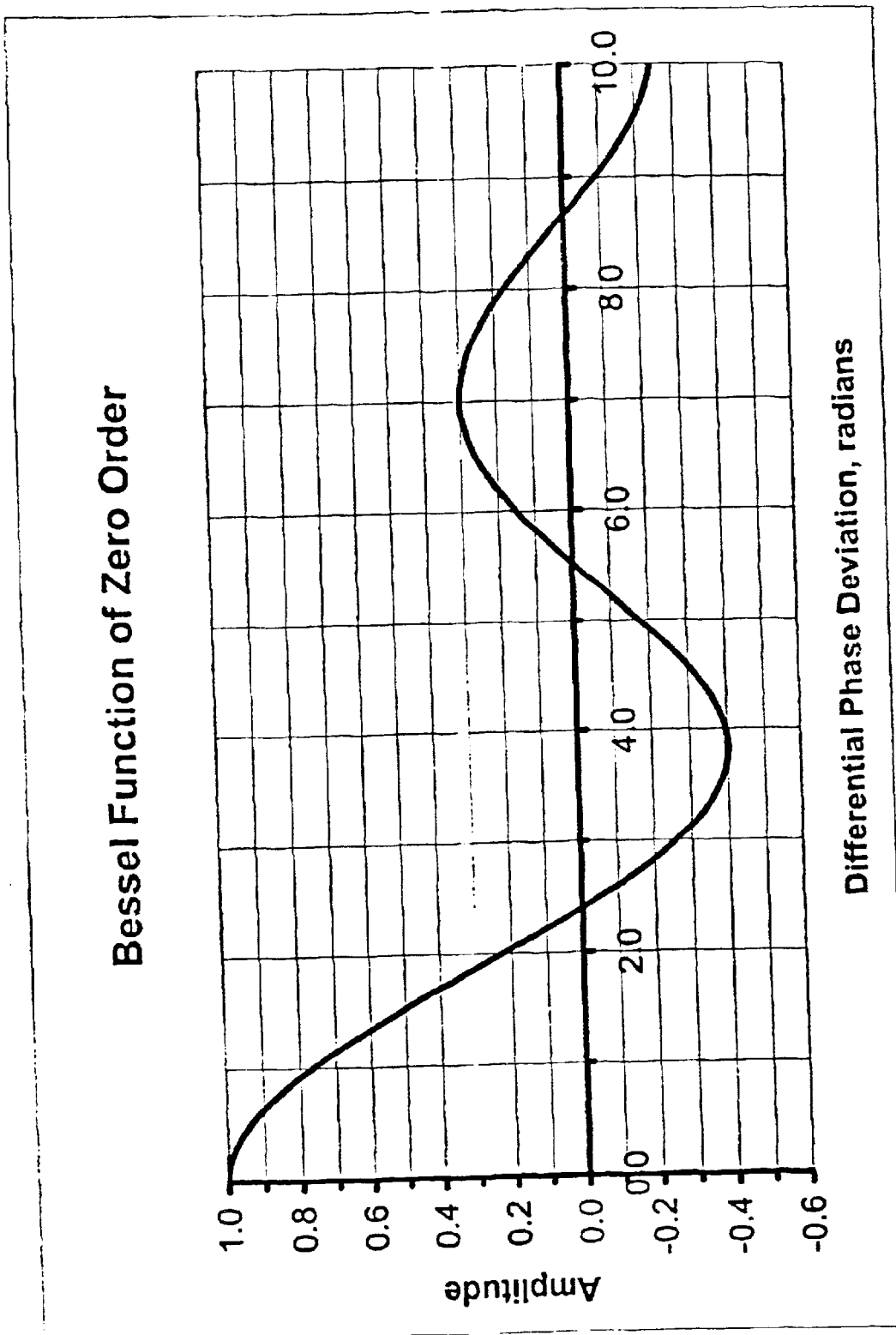
FIG. 26 is a graph of a zero order bessel function showing amplitude as a function of differential phase deviation.

In relation to the Bessel function, interferometric noise and back reflection can be eliminated by two basic methods. The first technique employs phase modulation at relatively low radio frequencies, e.g., 1 MHz relative to the modulation frequencies of interest, in order to disperse the interferometric noise to the low radio frequencies (FIGS. 24(a)-(d). This method is referred to here as the "Low-Frequency Method". This technique works best if the single pass phase deviation Df is such that the $J_0(2Df)$ Bessel function is at or close to zero. This technique is also independent of optical fiber length. When the light in the optical fiber is phase modulated at a rate much higher than such that the modulation of interest and if the peak differential phase modulation between the direct optical signal and the third transit reflection is greater than V p/2, most of the interferometric noise energy can be dispersed out of band (FIGS. 24(a)-25(b). In this situation, the delay time of the optical reflection is very small compared to the period of the phase modulation frequency $f_m$. The Noise Reduction Factor or NRF is the multiplication factor by which the interferometric baseband noise is scaled. There is no reduction in noise when NRF=1 and there is a complete elimination in interferometric noise when NRF=0. The NRF for the low-frequency technique can be defined as:

$$NRF = J_0^2(2Df) \quad (3)$$

where $J_0(x)$=Bessel function of zero-order. This function is plotted in FIG. 26. This is a measure of the power in the optical carrier and appears in the DC component of the detected optical signal. As mentioned in FIG. 22, the total net phase distribution is $2Df_m$. As shown in FIG. 24(c), when 2Df=2.405 radians, the NRF=0 and the interferometric noise around the optical carrier frequency (noise around the biopotential signal, i.e. DC baseband frequencies) caused by interference between the direct optical signal and its third transit is effectively suppressed. The interferometric noise is moved to the vicinity of the harmonics of the phase modulation frequency. If the frequency of the phase modulating tone is outside the passband of the signal processing system of the electronic circuitry 60 (e.g., FIG. 1), then these harmonics and the associated interferometric noise will not be detected. FIGS. 24(a)-(d) thus illustrates the Bessel harmonics produced by phase modulation. With a phase modulation of 2.405 radians the amplitude of the carrier component is reduced to zero. The amplitudes of the harmonics of the phase modulation tone are shown on a relative linear scale. FIGS. 25(a)-(b) show the interferometric noise shifted from low frequencies to those frequencies centered about the phase modulation tone on a logarithmic scale.

The second technique, which also uses phase modulation, but at very high radio frequencies relies on producing a zero of the $J_0(Df2\sin[2pf_mt])$ Bessel function so that the interferometric noise is eliminated around the carrier frequency. Therefore the modulation frequency $f_m$, which may be in the hundreds of MHz or even GHz range, has to be precisely tuned for the round-trip delay t of the dominant optical reflection. This technique is referred to as the "High-Frequency Method". Defining the Noise Reduction Factor (NRF) for the high frequency technique, it can be shown that the NRF is given by:

$$NRF = J_0^2(2Df \sin[2pf_mt]) \quad (4).$$

Figure 27:
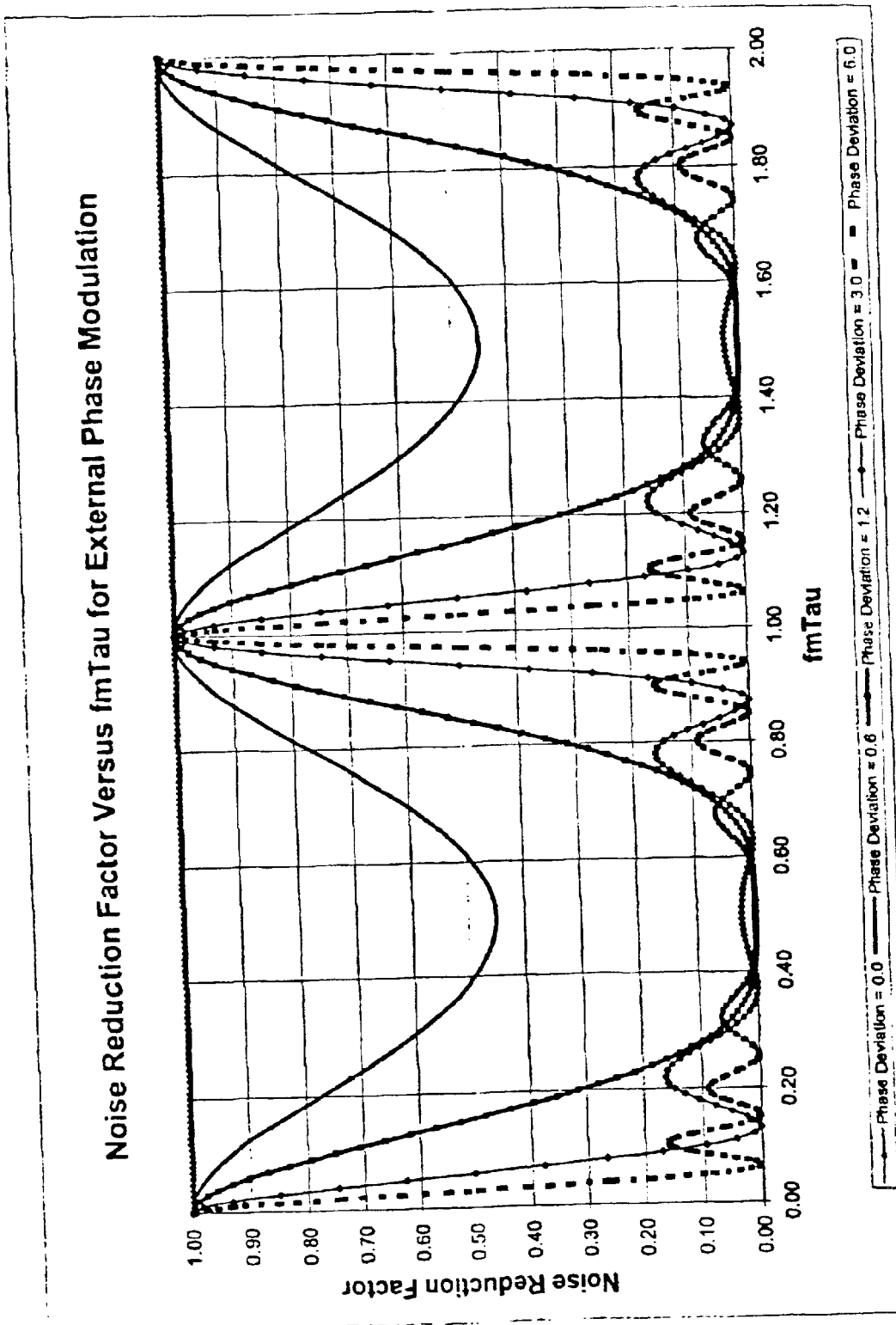
FIG. 27 is a graph of the noise reduction faction for external phase modulation.

This function is maximum when $f_mt$=0, 1, 2, 3, etc. It is a minimum when Df=1.2025 and $f_mt$=0.5, 1.5, 2.5, etc. There are also in-between values of $f_mt$ that will make the NRF=0 when Df is a multiple of 1.2025. The value 2Df= 2.405 will be recognized as the first zero of the Bessel function $J_0(2Df)$. If the modulation frequency $f_m$ is chosen correctly to match the round-trip delay time t, then the NRF can be at or close to zero, providing the maximum amount of back noise suppression. FIG. 27 shows how the NSF depends on the $tf_m$ and Df. The first zero for a minimum phase deviation of 1.2025 is for $f_mt$=0.5. Assuming that there is only one major optical reflection, the phase modulation frequency $f_m$ is adjusted until the baseband interferometric noise is minimized (first minima). Since the refractive index of an optical fiber is about 1.48, the velocity of light along a fiber is about $2.03 \times 10^8$ m/s and if the normal propagation delay, t, is about 0.5 ns/m, and the two reflection sections of the fiber are 1 meter apart the differential t=1 ns. Therefore the differential phase modulation 2Df=2.405 radians at a $f_m$=500 MHz will cause the NRF to be zero. Therefore this technique is dependant on the optical fiber length.

EXAMPLE I

Figure 28:
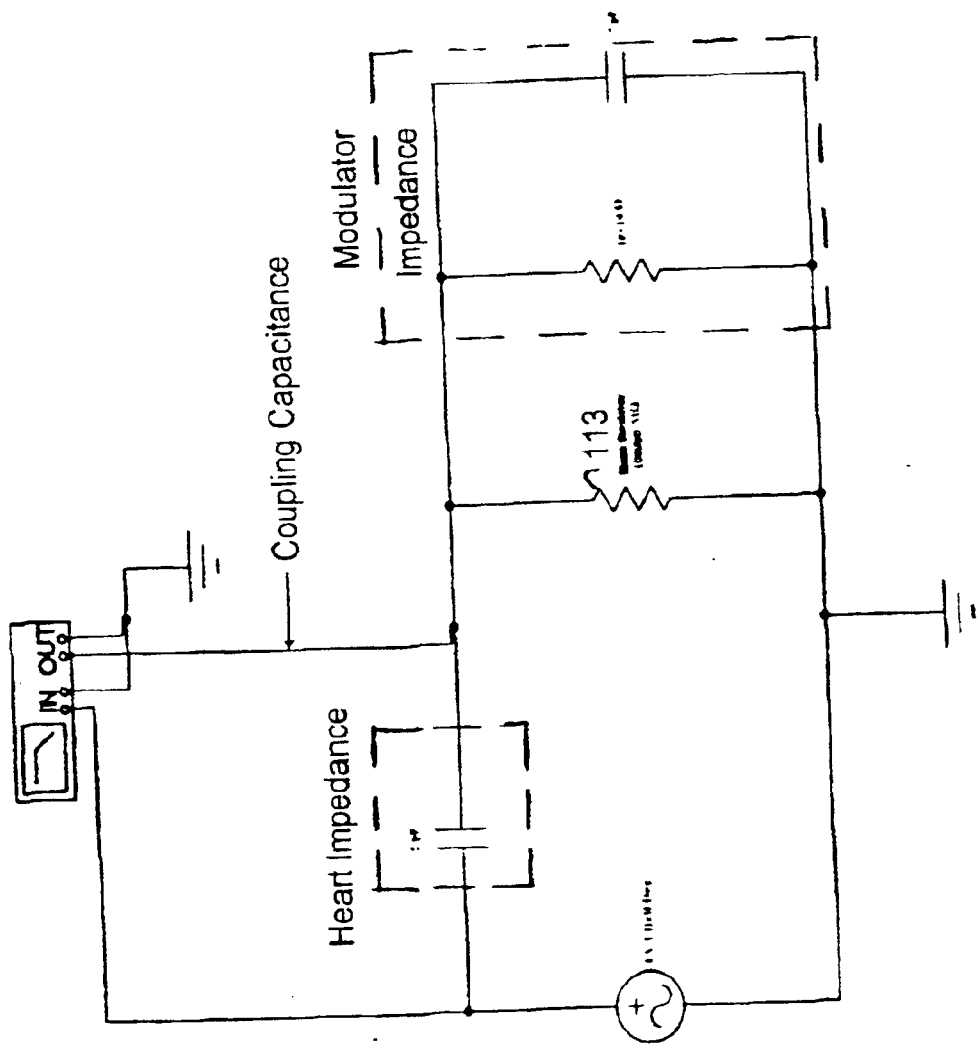
FIG. 28 is a schematic diagram showing the equivalent impedance of the electro-optic modulator with respect to the heart placement.

Conventional practice for attaining ECG signals requires removal of clothing as well as application of an electrolyte gel. In the present invention, ECG recordings are taken without removal of clothing thereby eliminating the need for electrolyte gel and also providing optimum comfort to the patient undergoing testing. The ECG is measured by placing the electro-optic modulator 30 on the heart (over the clothes) in the left leg/right ventricle position as seen in FIG. 7. FIG. 28 shows the equivalent impedance of the device 30 with respect to the heart placement. The shunting resistor 113 is shown to have a value of 100 GW thereby increasing the DC stability of the device 30. Since the ECG signal coupling can be capacitive in nature, the signal may also be detected without the use of conducting silicon and with a simple metal electrode, or disk for contact with the skin. A notch filter (not shown) was used in order to block the effects of 60 Hz environmental fields on the ECG waveform. The electro-optic modulator 30 with its integrated optic fiber and electro-optic field sensing allows for low risk, rapid, non-contact monitoring of the heart's induced bio-electric potential. This device allows for monitoring of vital signs in a safe, effective, and non-invasive manner. Also, due to its high impedance nature, skin moisture will not affect the electrode thereby eliminating all need for skin preparation as well as eliminating the need for a designated hospital environment.

Figure 29:
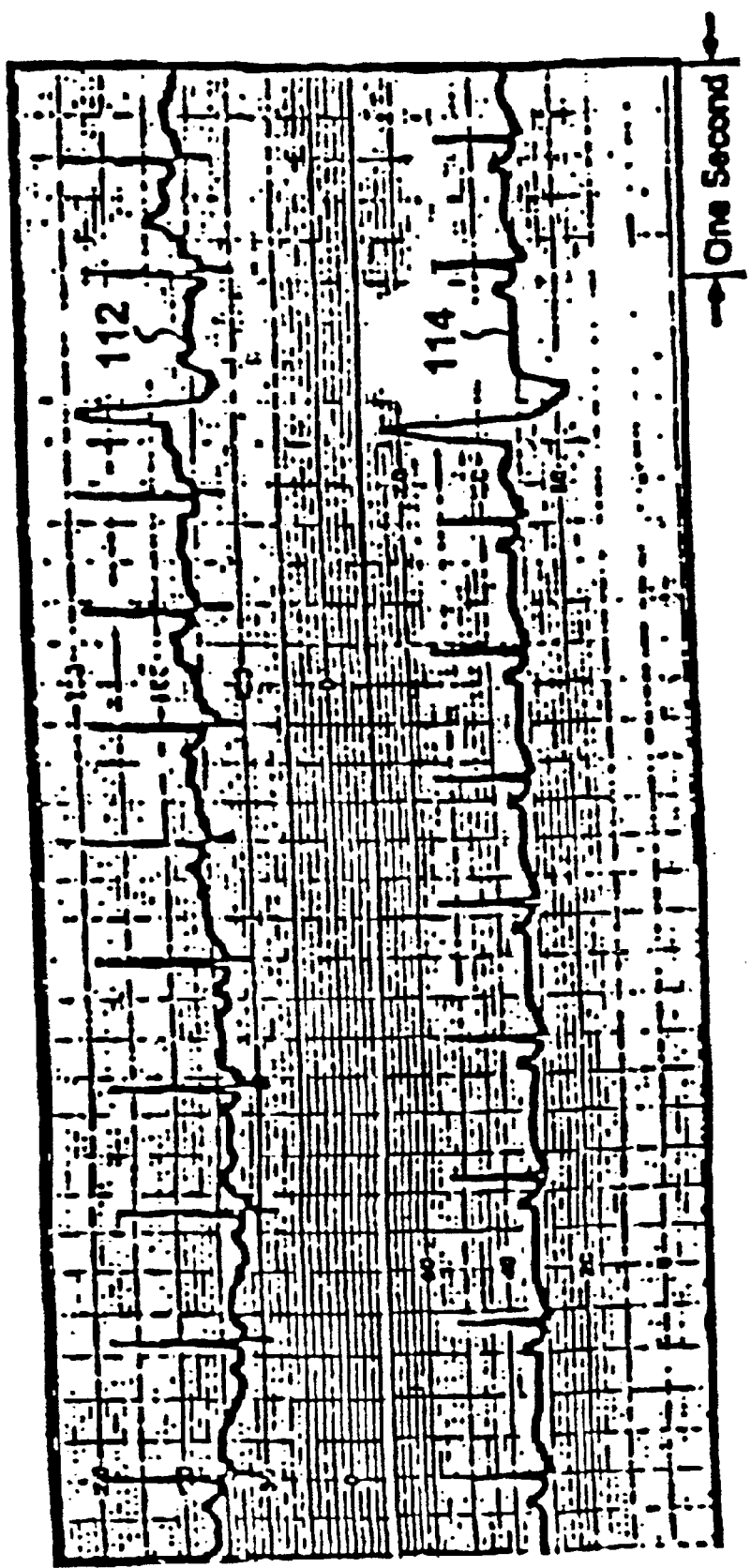
FIG. 29 gives two output ECG traces, the upper trace was taken with the high-impedance optical electrode of the current invention while the lower trace is taken with conventional electrodes.

FIG. 29 shows the high impedance trace 112 taken using the electro-optic modulator 30 of the current invention as compared to a trace 114 taken with standard low impedance electrodes (Life Patch Physio-Control Corporation Redmond, Wash.) that are used routinely to take ECG readings in hospital environments (Physio-Control Life Pack VSM1 Graphic Controls, Buffalo, N.Y.). Waveform 112 expresses the R, S, and T waves predominantly, the amplitude is greater than the standard system, and thus able to be further studied and applied especially when determining the polarization of a patient's heart. Comparing the two waveform traces, the patients' arrhythmia can clearly be seen on both traces.

EXAMPLE II

Figure 31:
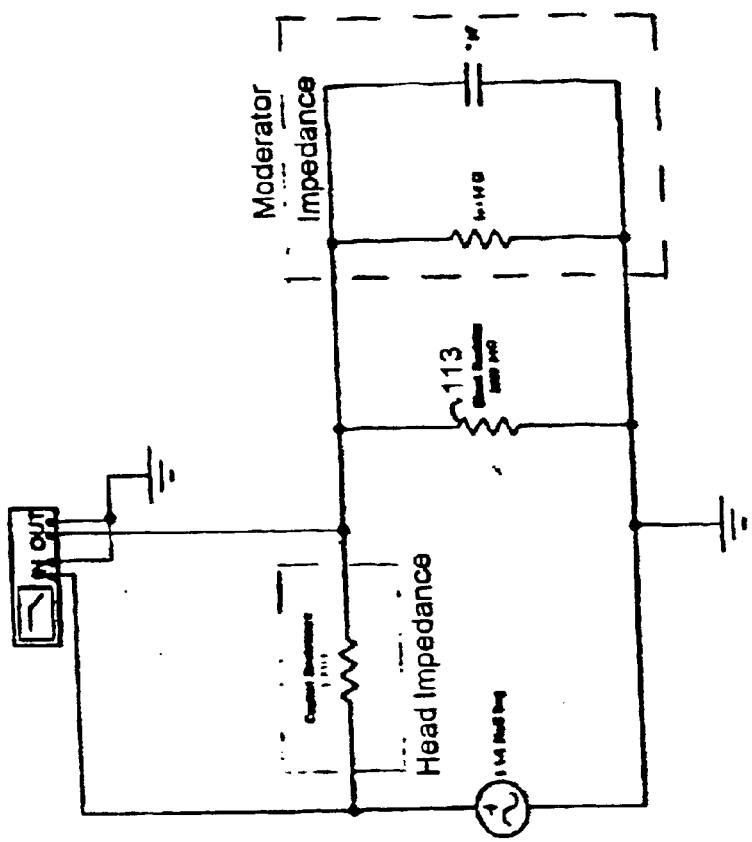
FIG. 31 shows the equivalent impedance of the EEG with respect to the electro-optic device.
Figure 30:
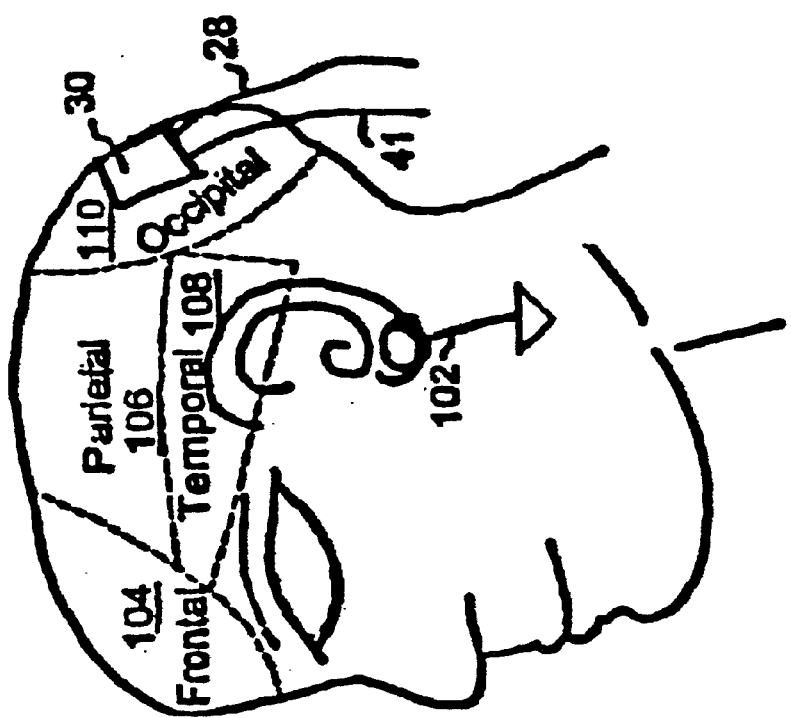
FIG. 30 is a side view of the head of a patient showing major areas of bio-potential activity and placement of an electrode for measuring alpha wave activity and an ear lobe grounding electrode.
Figure 32:
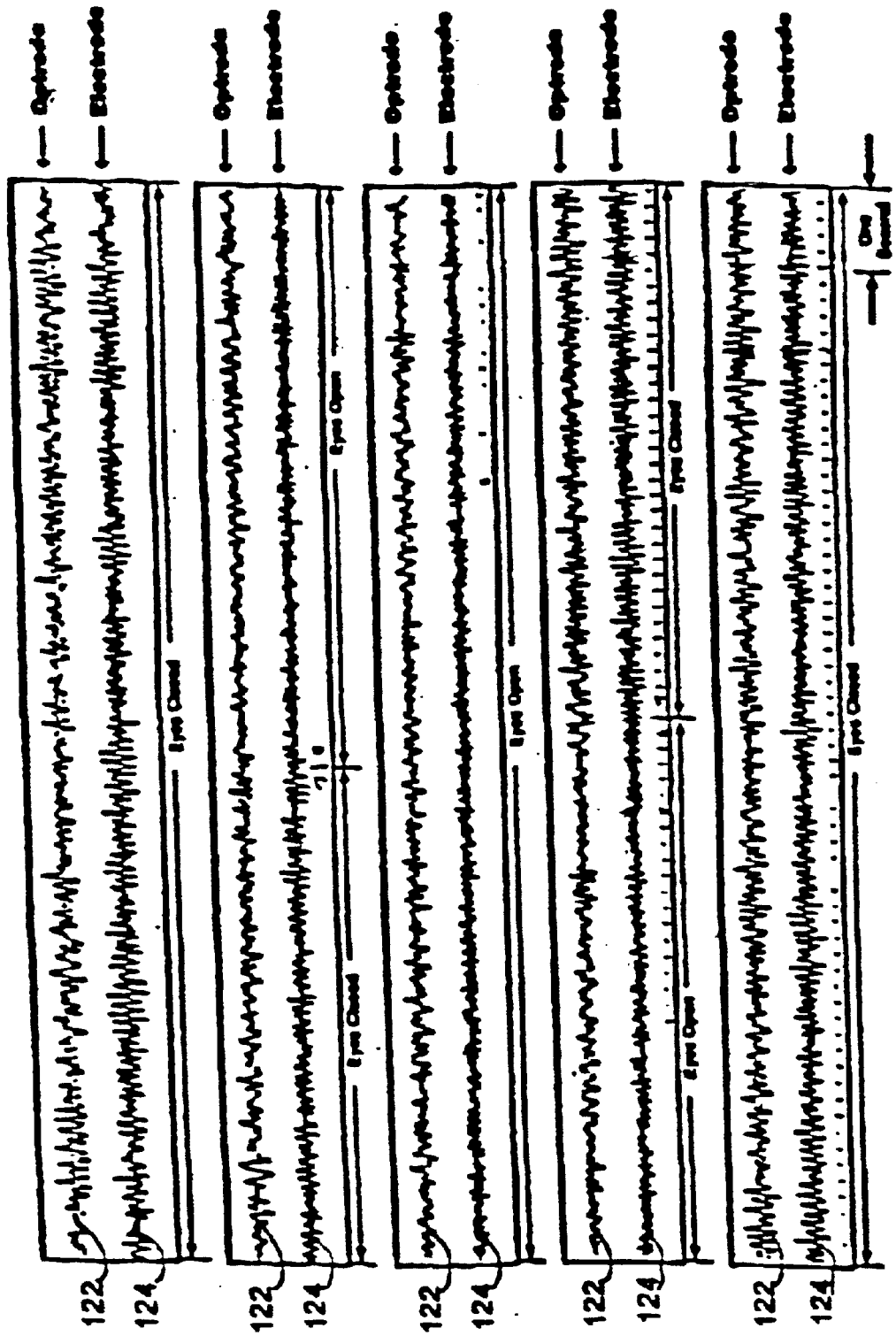
FIG. 32 gives alpha wave traces using the high-impedance optical electrode of the current invention and standard electrodes with the current invention trace given at the top of each trace strip and the standard electrode given at the bottom of each trace.

Traces taken with the electro-optic module of the current invention of EEG activity is very similar to low impedance electrode data. The EEG pattern is typical of a normal subject showing the eyes open and closed response. As an example, a single electrode (E5GH Astro-Medical Inc. West Warwick, R.I.), and an electro-optic module of the present invention were placed on the occipital lobe 110 in order to measure the brain's alpha wave activity (FIG. 30). FIG. 31 shows the equivalent impedance of the EEG with respect to the device 30. The shunting resistor 113 is shown having a value of 1 GW and thus improves the DC stability of the device 30. A reference electrode 102, such as the Life-Patch, was attached to the ear for grounding purposes. The standard EEG electrode required abrading the patients scalp with acetone whereas the electrode of the current invention 30 required no abrasion techniques. Colloid was applied to the standard electrode in order to get the electrode to stick to the surface of the patient's scalp. In addition to the colloid, electrolyte gel had to be applied to the standard electrode to obtain sufficient conductivity. The EEG alpha wave patterns were recorded (Physio-Control Life Pack VSM1) using the standard electrode and the electro-optic modulator 30 and then compared. Results for a standard electrode 124 and those obtained with the current invention 122 for the alpha wave are seen in FIG. 32. The EEG signal can also be measured using from one to twenty-four electrodes, using the International Federation 10-20 system.

In conclusion, the overall device and method of measuring ECG and EEG signals of the current invention is an improvement from the standard techniques used to this day. It is to be noted that other bio-potentials could be measured in addition to those discussed with the same optical modulators of the current invention. The unique features to the present invention method include 1) a dry, high-impedance contact requiring no special or abrading skin preparation or conducting gels, 2) low cost comparable with commercially available system, 3) reusable nature, 4) the avoidance of macro-shock and burns, 5) low power consumption, 6) small size required to fit multiple modulators into small areas, 7) capability to measure bio-potentials available at various frequencies, 8) easy set up, and 9) compatibility with standard, commercially available filtering, amplification, hardware, and software programs.

It is possible that changes in configurations to other than those shown could be used but that which is shown is preferred and typical. Without departing from the spirit of this invention, various equivalent electronic components and interconnection may be used.

It is therefore understood that although the present invention has been specifically disclosed with the preferred embodiment and examples, modifications to the design concerning selection of individual components and their interconnection will be apparent to those skilled in the art and such modifications and variations are considered to be equivalent to and within the scope of the disclosed invention and the appended claims.

We claim:

1. A high-impedance optical electrode used for measuring bio-potentials comprising:
    a) a light source;
    b) an electro-optic modulator:
        (1) receiving light from said light source;
        (2) modulating said light in response to a bio-potential; and
        (3) providing a modulated light output proportional to said bio-potential;
    c) a photodetector for receiving and converting said modulated light output from said electro-optic modulator to an electrical signal;
    d) electronic circuitry for providing an electronic output signal; and
    e) a pilot tone generated by said electronic circuitry and superimposed on said bio-potential.

2. A high-impedance optical electrode used for measuring bio-potentials comprising:
    a) a light source;
    b) an electro-optic modulator:
        (1) receiving light from said light source;
        (2) modulating said light in response to a bio-potential; and
        (3) providing a modulated light output proportional to said bio-potential;
    c) an optical splitter for splitting said light from said light source into at least a second light portion wherein said second light portion is used as an optical reference signal.

3. The high-impedance optical electrode used for measuring bio-potentials according to claim 2 wherein said second a third light portion is received by a second electro-optical modulator.

4. The high-impedance optical electrode used for measuring bio-potentials according to claim 2 further comprising an optical phase-shift modulator.

5. A high impedance optical electrode for measuring bio-potentials comprising:
    a) a light source;
    b) a bio-potential;
    c) an electro-optic modulator;
        (1) receiving light from said light source;
        (2) modulating said light in response to a bio-potential; and
        (3) providing a modulated light output;
    d) a photodetector for receiving and converting said modulated light output from said electro-optic modulator into an electrical output; and
    e) wherein at least one end of said electro-optic modulator connections to at least one member of a group of members consisting of: an optical fiber, said light source, and said photodetector, is formed at an angle to vertical.

6. The high impedance optical electrode according to claim 5 wherein said electrical output is a voltage.

7. The high impedance optical electrode according to claim 5 wherein said light source is a laser diode.

8. The high impedance optical electrode according to claim 7 wherein said laser diode is a highly coherent laser diode.

9. The high impedance optical electrode according to claim 7 wherein said laser diode is a low coherent laser diode.

10. The high impedance optical electrode for measuring bio-potentials according to claim 5 wherein said light source is a distributed feedback laser.

11. The high impedance optical electrode for measuring bio-potentials according to claim 5 wherein said light source is a Fabry-Perot laser.

12. The high impedance optical electrode for measuring bio-potentials according to claim 5 wherein said light source is a vertical cavity surface-emitting laser.

13. The high impedance optical electrode for measuring bio-potentials according to claim 5 wherein said light source is connected to said electro-optic modulator with an optical fiber.

14. The high impedance optical electrode for measuring bio-potentials according to claim 5 wherein said electrooptic modulator is connected to said photodetector with an optical fiber.

15. The high impedance optical electrode for measuring bio-potentials according to claim 13 wherein said electro-optic modulator is connected to said photodetector with an optical fiber.

16. The high impedance optical electrode for measuring bio-potentials according to claim 5 wherein at least one end of said electro-optic modulator is connected to an optical fiber with an optical carrier.

17. The high impedance optical electrode for measuring bio-potentials according to claim 16 wherein an end of said optical carrier connected to said electro-optic modulator is formed at an angle to vertical.

18. A high impedance optical electrode for measuring bio-potentials comprising:
   a) a light source;
   b) a bio-potential;
   c) an electro-optic modulator;
      (1) receiving light from said light source;
      (2) modulating said light in response to a bio-potential; and
      (3) providing a modulated light output;
   d) a photodetector for receiving and converting said modulated light output from said electro-optic modulator into an electrical output; and
   e) wherein at least said electro-optic modulator is enclosed in a housing at least partially covered with electro-magnetic shielding wherein said electro-magnetic shielding is a conductive paint.

19. The high impedance optical electrode for measuring bio-potentials according to claim 18 wherein said housing is hermetically sealed.

20. The high impedance optical electrode for measuring bio-potentials according to claim 18 wherein said housing provides a ground return.

21. A high impedance optical electrode for measuring bio-potentials comprising:
   a) a light source;
   b) a bio-potential;
   c) an electro-optic modulator;
      (1) receiving light from said light source;
      (2) modulating said light in response to said bio-potential; and
      (3) providing a modulated light output;
   d) wherein said electro-optic modulator is a Mach-Zehnder interferometer comprising a substrate having formed therein:
      (1) a light input wave-guide receiving light from said light source;
      (2) a splitter connected to said light input wave-guide;
      (3) a first leg light wave-guide connected to said splitter;
      (4) a second leg light wave-guide connected to said splitter;
      (5) a combiner connected for receiving light from said first leg light wave-guide and said second leg light wave-guide; and
      (6) a light output wave-guide connected to said combiner;
      (7) a bio-potential plate mounted on said substrate between said first leg light wave-guide and said second light wave-guide;
      (8) a first grounding plate mounted on said substrate on a side of said first leg light wave-guide opposite said bio-potential plate;
      (9) a second grounding plate mounted on said substrate on a side of said second leg light wave-guide opposite said bio-potential plate;
      (10) a pick-up pad electrically connected to said bio-potential plate; and
   e) a photodetector for receiving and converting said modulated light output from said electro-optic modulator into an electrical output.

22. The high impedance optical electrode for measuring bio-potentials according to claim 21 wherein said Mach-Zehnder interferometer operates in a linear region.

23. The high impedance optical electrode for measuring bio-potentials according to claim 21 wherein said substrate is crystalline.

24. The high impedance optical electrode for measuring bio-potentials according to claim 21 wherein said crystalline substrate comprises $LiNbO_3$.

25. The high impedance optical electrode for measuring bio-potentials according to claim 21 wherein said grounding plates are connected to a ground return provided by a housing.

26. The high impedance optical electrode for measuring bio-potentials according to claim 21 further comprising a shunt resistor connected to said bio-potential plate and said grounding plate.

27. A high impedance optical electrode for measuring bio-potentials comprising:
   a) a light source;
   b) a bio-potential;
   c) an electro-optic modulator;
      (1) receiving light from said light source;
      (2) modulating said light in response to said bio-potential; and
      (3) providing a modulated light output;
   d) wherein said electro-optic modulator is a Mach-Zehnder interferometer comprising a substrate having formed therein:
      (1) a light input wave-guide receiving light from said light source;
      (2) a splitter connected to said light input wave-guide;
      (3) a first leg light wave-guide connected to said splitter;
      (4) a second leg light wave-guide connected to said splitter;
      (5) a combiner connected for receiving light from said first leg light wave-guide and said second leg light wave-guide; and
      (6) a light output wave-guide connected to said combiner; and
   e) a photodetector for receiving and converting said modulated light output from said electro-optic modulator into an electrical output; and
   f) a spatial filter mounted to an end of said substrate.

28. The high impedance optical electrode for measuring bio-potentials according to claim 21 further comprising a strap for securing said electro-optic modulator to a patient.

29. The high impedance optical electrode for measuring bio-potentials according to claim 27 further comprising a helmet for positioning said electro-optic modulator on a patient.

30. The high impedance optical electrode for measuring bio-potentials according to claim 29 wherein said helmet provides a ground return for said electro-optic modulator.

31. A high impedance optical electrode for measuring bio-potentials comprising:
   a) a light source;
   b) a bio-potential;
   c) an electro-optic modulator;
      (1) receiving light from said light source;
      (2) modulating said light in response to a bio-potential; and
      (3) providing a modulated light output;
   d) a photodetector for receiving and converting said modulated light output from said electro-optic modulator into an electrical output; and e) a bio-potential plate for receiving said bio-potential and modulating said light in response thereto.

32. The high impedance optical electrode for measuring bio-potentials according to claim 31 wherein said bio-potential plate is electrically connected to a pick-up pad for acquiring said bio-potential.

33. The high impedance optical electrode for measuring bio-potentials according to claim 32 wherein said pick-up pad is used without conductive ointments.

34. The high impedance optical electrode for measuring bio-potentials according to claim 32 wherein said pick-up pad has an irregular surface.

35. The high impedance optical electrode for measuring bio-potentials according to claim 32 with said pick-up pad comprising an electrically conducting disk.

36. The high impedance optical electrode for measuring bio-potentials according to claim 32 wherein said pick-up pad is mounted to a housing for said electro-optic modulator.

37. The high impedance optical electrode for measuring bio-potentials according to claim 31 wherein said bio-potential plate receives said bio-potential through clothing.

38. The high impedance optical electrode for measuring bio-potentials according to claim 31 wherein said bio-potential plate receives said bio-potential as a result of capacitive coupling.

39. The high impedance optical electrode for measuring bio-potentials according to claim 31 further comprising of an optical power splitter for receiving light from said light source and providing said light to at least two light receiving devices.

40. The high impedance optical electrode for measuring bio-potentials according to claim 39 wherein one of said light-receiving devices is a second photodetector.

41. The high impedance optical electrode for measuring bio-potentials according to claim 40 wherein said second photodetector is a reference photodetector.

42. The high impedance optical electrode for measuring bio-potentials according to claim 39 wherein one of said light receiving devices is a second electro-optic modulator.

43. The high impedance optical electrode for measuring bio-potentials according to claim 39 wherein said optical splitter comprises an N-splitter.

44. The high impedance optical electrode for measuring bio-potentials according to claim 39 wherein said optical splitter comprises an X:Y splitter.

45. The high impedance optical electrode for measuring bio-potentials according to claim 31 further comprising a phase modulator receiving light from one of the light source and said electro-optic modulator.

46. The high impedance optical electrode for measuring bio-potentials according to claim 45 with said phase modulator comprising a piezo-electric substrate having formed therein a light waveguide with a hot electrode and a ground electrode mounted opposite each other on each side of said waveguide.

47. The high impedance optical electrode for measuring bio-potentials according to claim 46 further comprising a frequency generator for imposing a potential on said hot electrode with a frequency higher than a frequency range of said bio-potential.

48. The high impedance optical electrode for measuring bio-potentials according to claim 31 further comprising electronic circuitry for processing said electrical output from said photodetector.

49. The high impedance optical electrode for measuring bio-potentials according to claim 48 with said electronic circuitry comprising post photodetector processing.

50. The high impedance optical electrode for measuring bio-potentials according to claim 48 with said electronic circuitry comprising DC transient suppression circuitry.

51. The high impedance optical electrode for measuring bio-potentials according to claim 48 with said electronic circuitry comprising amplification circuitry.

52. The high impedance optical electrode for measuring bio-potentials according to claim 48 with said electronic circuitry comprising filtering circuitry.

53. The high impedance optical electrode for measuring bio-potentials according to claim 48 with said electronic circuitry comprising pilot tone generation circuitry.

54. The high impedance optical electrode for measuring bio-potentials according to claim 48 wherein a pilot tone from said pilot tone generation circuitry is superimposed on said bio-potential at a frequency outside of the frequency range of said bio-potential.

55. The high impedance optical electrode for measuring bio-potentials according to claim 54 wherein said pilot tone is applied directly to a patient.

56. An optical electrode for measuring bio-potentials comprising:
   a) a low coherent laser diode light source;
   b) a bio-potential;
   c) an electro-optic modulator;
      (1) receiving light from said light source;
      (2) modulating said light in response to a bio-potential; and
      (3) providing a modulated light output;
   d) a photodetector for receiving and converting said modulated light output from said electro-optic modulator into an electrical output.

* * * * *

UNITED STATES PATENT AND TRADEMARK OFFICE
CERTIFICATE OF CORRECTION

PATENT NO. : 6,871,084 B1
DATED : March 22, 2005
INVENTOR(S) : Kingsley et al.

It is certified that error appears in the above-identified patent and that said Letters Patent is hereby corrected as shown below:

Column 9,
Line 51, after "two" add -- or --.

Column 10,
Line 40, after "that" delete "carrier" and insert -- carries --.
Line 56, after "physical" delete "contract" and insert -- contact --.

Column 12,
Line 40, after "minimize" delete "patent" and insert -- patient --.

Column 13,
Line 5, after "is" delete "make" and insert -- made --.
Line 45, after "is" delete "titled" and insert -- tilted --.

Column 15,
Line 65, the equation should read:
-- CNR = hP/2hfB --.

Column 17,
Line 13, after "1-100" delete "IIz" and substitute -- Hz --.
Line 53, after "FIG." delete "15e" and substitute -- 15f --.

Column 22,
Line 13, delete "MIIz" and substitute -- MHz --.

Column 24,
Lines 13-14, after "wherein" delete "said second".
Line 33, "connections" should be -- connected --.

UNITED STATES PATENT AND TRADEMARK OFFICE
CERTIFICATE OF CORRECTION

PATENT NO. : 6,871,084 B1
DATED : March 22, 2005
INVENTOR(S) : Kingsley et al.

It is certified that error appears in the above-identified patent and that said Letters Patent is hereby corrected as shown below:

<u>Column 26,</u>
Line 47, after "to" "claim 21" should be -- claim 27 --.

Signed and Sealed this

Thirtieth Day of May, 2006

JON W. DUDAS
*Director of the United States Patent and Trademark Office*